(12) United States Patent
Yang et al.

(10) Patent No.: US 7,316,816 B2
(45) Date of Patent: Jan. 8, 2008

(54) TEMPERATURE AND PH SENSITIVE COPOLYMERS

(75) Inventors: Yi-Yan Yang, Singapore (SG); Kumaresh Soppimath, Singapore (SG)

(73) Assignee: Agency for Science Technology and Research, Singapore (SG)

( * ) Notice: Subject to any disclaimer, the term of this patent is extended or adjusted under 35 U.S.C. 154(b) by 237 days.

(21) Appl. No.: 10/865,681

(22) Filed: Jun. 10, 2004

(65) Prior Publication Data

US 2005/0277739 A1  Dec. 15, 2005

(51) Int. Cl.
 A61K 47/32 (2006.01)
(52) U.S. Cl. ............... 424/427; 424/486; 424/489; 424/78.01; 424/78.18; 424/78.31; 424/78.35; 525/242; 525/317.1; 526/258; 526/265; 526/303.1; 526/307.6
(58) Field of Classification Search ............... 525/242; 526/258, 265, 303.1, 307.6, 317.1; 424/427, 424/486, 489, 78.01, 78.18, 78.31, 78.35
See application file for complete search history.

(56) References Cited

U.S. PATENT DOCUMENTS

| | | | | |
|---|---|---|---|---|
| 3,925,542 | A * | 12/1975 | Viout et al. | .............. 424/47 |
| 4,675,362 | A | 6/1987 | Miyabayashi et al. | |
| 5,108,568 | A | 4/1992 | Van Alstine | |
| 5,226,902 | A * | 7/1993 | Bae et al. | ............ 604/892.1 |
| 6,197,522 | B1 * | 3/2001 | Keller et al. | ............ 435/7.1 |
| 2004/0010080 | A1 | 1/2004 | Hutter et al. | |

FOREIGN PATENT DOCUMENTS

| | | |
|---|---|---|
| WO | WO 01/87227 | 11/2001 |
| WO | WO 2004/096140 | 11/2004 |

OTHER PUBLICATIONS

Allen et al., "Nano-engineering block copolymer aggregates for drug delivery," *Colloids and Surfaces B: Biointerfaces*, 16:3-27 (1999).
Bokias, et al., "Molar mass control of poly(N-isopropylacrylamide) and poly(acrylic acid) in aqueous polymerizations initiated by redox initiators based on persulfates," *Macromol. Chem.Phys.*, 199:1387-1392 (1998).
Chen and Hoffman, "Graft copolymers that exhibit temperature-induced phase transitions over a wide range of pH," *Nature*, 373:49-52 (1995), (Abstract only).
Chung, et al., "Thermo-responsive drug delivery from polymeric micelles constructed using block copolymers of poly(N-isopropylacrylamide) and poly(butylmethacrylate)," *Journal of Controlled Release*, 62:115-127 (1999).
Drummond, et al., "Current status of pH-sensitive liposomes in drug delivery," *Progress in Lipid Research*, 39:409-460 (2000).
Gregg, et al., "Chain Transfer in the Polymerization of Styrene. V. Polymerization of Styrene in the Presence of Mercaptans," [Contribution No. 77 from the General Laboratories of the United States Rubber Company], 70:3740-3743 (1948).
Kabanov, et al., "The neuroleptic activity of haloperidol increases after its solubilization in surfactant micelles," *FEBS Letters*, 258(2):343-345 (1989).
Kataoka, et al., "Block copolymer micelles for drug delivery: design, characterization and biological significance," *Advanced Drug Delivery Reviews*, 47:113-131 (2001).
Katsumoto, et al., "Conformational Change of Poly(N-isopropylacrylamide) during the Coil-Globule Transition Investigated by Attenuated Total Reflection/Infrared Spectroscopy and Density Functional Theory Calculation," *J. Phys. Chem.*, 106:3429-3435 (2002).
Kohori, et al., "Control of adriamycin cytotoxic activity using thermally responsive polymeric micelles composed of poly(N-isopropylacrylaminde-co-N, N-dimethylacrylamide)-b-poly(D,L-lactide)," *Colloids and Surfaces*, 16:195-205 (1999).
Lee, et al., "Polymeric micelle for tumor pH and folate-mediated targeting," *Journal of Controlled Release*, 91:103-113 (2003).
Lee, et al., "Poly(L-histidine)-PEG block copolymer micelles and pH-induced destabilization," *Journal of Controlled Release*, 90:363-374 (2003).
Liu and Liu, "Synthesis and Characterization of Temperature- and pH- Sensitive Poly(N,N-diethylacrylamide-co-methacrylic acid)," *Journal of Applied Polymer Science*, 90:3563-3568 (2003).
Matsumuara and Maeda, "A new concept for macromolecular therapeutics in cancer chemotherapy: mechanism of tumoritropic accumulation of proteins and the antitumor agent smancs," *Cancer Research*, 46(12):6387-6392 (1986).
Stile and Healy, "Poly(N-isopropylacrylamide)-Based Semi-interpenetrating Polymer Networks for Tissue Engineering Applications. 1. Effects of Linear Poly(acrylic acid) Chaims on Phase Behavior," *Biomacromolecules*, 3:591-600 (2002).
Torchilin, V., "Structure and design of polymeric surfactant-based drug delivery systems," *Journal of Controlled Release*, 73:137-172 (2001).
Vaupel, et al., "Heterogeneous oxygen partial pressure and pH distribution in C3H mouse mammary adenocarcinoma," *Cancer Research*, 41(5):2008-2013 (1981), (Abstract only).
Dong and Winnik, "The Py scale of solvent polarities." Can.J. Chem., 62:2560-2565, 1984.

(Continued)

*Primary Examiner*—Jeffrey Mullis
(74) *Attorney, Agent, or Firm*—Foley & Lardner, LLP

(57) ABSTRACT

The invention is directed to a copolymer comprising at least three types of monomeric units, said three types of monomeric units comprising:
 a temperature-sensitive unit,
 a hydrophilic unit, and
 a hydrophobic unit comprising at least one pH-sensitive moiety;
wherein said hydrophobic monomeric unit is derived from a copolymerisable unsaturated fatty acid.

40 Claims, 31 Drawing Sheets

OTHER PUBLICATIONS

Khune et al., "Synthesis and evaluation of N-substituted acrylamide polymers for enhanced oil recovery." Polym. Pryr. 22:76-77, 1981.

Lessard et al., "Effect of the molecular weight on the lower critical solution temperature of poly(N,N-diethylacrylamide) in aqueous solutions." Can.J.Chem., 79:1870-1874, 2001.

Taylor and Cerankowski, "Preparation of films exhibiting a balanced temperature dependence to permeation by aqueous solutions-A Study of lower consolute behavior." Journal of Polymer Science, 13:2551-2570, 1975.

Roux et al., Serum-stable and long-circulating, PEGylated, pH-sensitive liposomes. Journal of Controlled Release, 94:447-451, 2004.

International Search Report from Application No. PCT/SG2005/000164 dated Jul. 7, 2005.

* cited by examiner

Scheme 1

| Polymers | NIPAAm/ DMAAm/ UA (feed molar ratio) | CTA (mol %) | $M_w, M_n$[1] $(M_w/M_n)$ | $T_g$[2] (°C) | NIPAAm/ DMAAm/ (actual molar ratio)[3] | Acidity (mg NaOH/g)[4] | Thermal degradation (onset temp °C)[5] |
|---|---|---|---|---|---|---|---|
| Polymer I | 4.00:1.00:0.5 | 0.2 | 30804,19185 (2.02) | 133.0 | 4.17:1.00 | 8.0 | 437.8 |
| Polymer II | 3.75:1.25:0.5 | 0.4 | 9303, 5209 (1.78) | 134.4 | 3.62:1.25 | 9.68 | 458.8 |
| Polymer III | 3.50:1.50:0.5 | 0.4 | 11090,6374 (1.73) | 135.1 | 3.13:1.50: | 8.80 | 437.8 |

[1] Determined by GPC; [2] Determined by DSC; [3] Estimated by $^1$H NMR; [4] Estimated by acid-base titration; [5] Estimated by TGA Table 1

Scheme 4

Scheme 5

Scheme 6

TEMPERATURE AND PH SENSITIVE COPOLYMERS

This invention relates to novel copolymers, in particular, temperature- and pH-sensitive amphiphilic copolymers. The invention also relates to compositions comprising novel copolymers which are useful for drug delivery, as well as to methods of providing a selected therapeutic agent to an animal or human.

BACKGROUND OF THE INVENTION

The development of sophisticated pharmaceutical products and drug delivery methods that can provide precise targeting, timing and dosing of therapeutic drugs has been necessitated in part by complex requirements in the treatment of organ-specific disorders due to diseases such as cancer, HIV/AIDS, cystic fibrosis, etc. Some of the contributing factors to the complex requirements of treatment include the toxicity of drugs used in the treatment of such diseases, limited therapeutic activity of the drugs, as well as the inaccessibility and heterogeneity of the diseased organ.

Progress has been made in the delivery of drugs, particularly in the development of drug carriers showing low toxicity and which are capable of providing improved targeting of the diseased cells. Several types of drug carriers that provide improved drug delivery have been investigated, including liposomes, drug-polymer conjugates and nanoparticles.

Polymeric core-shell nanoparticles have emerged recently as promising colloidal carriers for targeting poorly water-soluble and amphiphilic drugs as well as genes to tumour sites [Kataoka et al.—Advanced Drug Delivery Rev. 47 (2001) 113-131; V. P. Torchilin—J. Control. Rel. 73 (2001) 137-172; Allen et al.—Cool. Surf. B: Biointerfaces 16 (1999) 3-27]. Polymeric core-shell nanoparticles are small in size, generally less than 200 nm, and can solubilize hydrophobic drugs, genes or proteins in their inner cores through hydrophobic interaction, electrostatic interaction and hydrogen bonding etc., while exposing their hydrophilic shells to the external environment. This effectively protects the enclosed bioactive compounds against degradation and enables them to exhibit prolonged activity in the systemic circulation by avoiding being scavenged by reticuloendothelial systems (RES). With polymeric core-shell nanoparticles, targeting can be achieved, both passively and actively,—through an enhanced permeation and retention effect (EPR effect) [Matsumura et al.—Cancer Research 46 (1986) 6387-6392] and the incorporation of recognition signals onto the surface of the micelles [Kabanov et al.—FEBS Lett. 258 (1989) 343-345] or introducing a polymer sensitive to variations in physiological environment such as temperature or pH.

Polymeric nanoparticles which have shells constructed from temperature-sensitive poly(N-isopropylacrylamide) (PNIPAAm) have recently attracted considerable attention because of the polymer's thermal responsiveness. PNIPAAm exhibits a lower critical solution temperature (LCST) of around 32° C. in aqueous solution, below which the polymer is water-soluble and above which the polymer is water-insoluble [Taylor et al.—J. Polym. Sci.: Polym. Chem. Ed. 13 (1975) 2551-2570]. The temperature-sensitivity of the polymer advantageously provides a means to target drug carriers thermally.

Okano et al. reported the synthesis of adriamycin-incorporated micellar structures derived from PNIPAAm-b-poly (butylmethacrylate) and PNIPAAm-b-poly(D,L-lactide) block copolymers [Chung et al.—J. Control. Rel. 62 (1999) 115-127; Kohori et al—Colloids and Surfaces B: Biointerfaces 16 (1999) 195-205]. The core-shell nanoparticles were well formed below LCST, but deformed at temperatures higher than LCST. The release of the drug was regulated through a combination of local heating and cooling cycles. However, it was found that temperature regulation alone was not efficient in targeting deep tissues or tumours.

One alternative to temperature sensitive drug carriers are pH-sensitive drug carriers. It is known, for example, that the extracellular pH of most solid tumours range from 5.7 to 7.8 [Vaupel et al.—Cancer Research 41 (1981) 2008-2013], while the pH of the tumour interstitial fluid rarely declines below pH 6.5. It is a challenge to provide a drug carrier with such a narrow pH window [Drummond et al.—Progress in Lipid Research 39 (2000) 409-460].

Chen and Hoffman reported the synthesis of a copolymer of NIPAAm and acrylic acid and its pH-dependent LCST, and proposed its possible application in drug targeting [Nature 373 (1995) 49-52]. More recently, core-shell nanoparticles made from poly(L-histidine)-b-poly(ethylene glycol) (PEG) were reported to be pH-sensitive, which released the enclosed drug, doxorubicin (DOX), at pH from 7.4 to 6.8 [Lee et al.—J. Control. Rel. 90 (2003) 363-374; J. Control. Rel. 91 (2003) 103-113]. The acidic environment triggered the destabilization of the core-shell nanoparticles and thus release the enclosed drug molecules at tumour tissues.

WO 01/87227 A2 discloses the use of a colloidal composition consisting of polymeric micelles having a hydrophobic core and a hydrophilic shell. The pH- and temperature-sensitive micelles are derived from a copolymer of NIPAAm, methacrylic acid and octadecyl acrylate. The temperature-sensitive and pH-sensitive moieties are located on the shell of micelles.

Despite the developments that have taken place, limitations in the current drug carriers still exist for which continuing efforts are needed to improve their performance.

Accordingly, it is an object of the present invention to provide polymeric compounds which can be used as drug carriers that have improved pH and temperature sensitivity, and thus provide improved drug delivery performance.

SUMMARY OF THE INVENTION

The present invention provides pH and temperature sensitive copolymers which can be used as materials for drug delivery. In one aspect, the invention is directed to a copolymer comprising at least three types of monomeric units, said three types of monomeric units comprising:
 a temperature-sensitive unit,
 a hydrophilic unit, and
 a hydrophobic unit comprising at least one pH-sensitive moiety;

wherein said hydrophobic monomeric unit is derived from a copolymerisable unsaturated fatty acid.

In another aspect, the invention is directed to a temperature and pH sensitive composition comprising:
 a therapeutic agent, and
 a copolymer comprising at least three types of monomeric units, said three
 types of monomeric units comprising:
  a temperature-sensitive unit,
  a hydrophilic unit, and
  a hydrophobic monomeric unit comprising at least one pH-sensitive
  moiety;

wherein said hydrophobic monomeric unit is derived from a copolymerisable unsaturated fatty acid.

In yet another aspect, the invention provides a method of providing a selected therapeutic agent to an animal or human, comprising administering to said animal or human a temperature and pH-sensitive composition comprising:
- a therapeutic agent, and
- a copolymer comprising at least three types of monomeric units, said three types of monomeric units comprising:
  - a temperature-sensitive unit,
  - a hydrophilic unit, and
  - a hydrophobic unit comprising at least one pH-sensitive moiety;
- wherein said hydrophobic monomeric unit is derived from a copolymerisable unsaturated fatty acid;

wherein said copolymer is arranged into at least one nanoparticle comprising a hydrophobic core and a hydrophilic shell; and wherein said therapeutic agent is contained within said hydrophobic core.

These aspects of the invention will be more fully understood in view of the following description, drawings and non-limiting examples.

DETAILED DESCRIPTION

Figure 1:
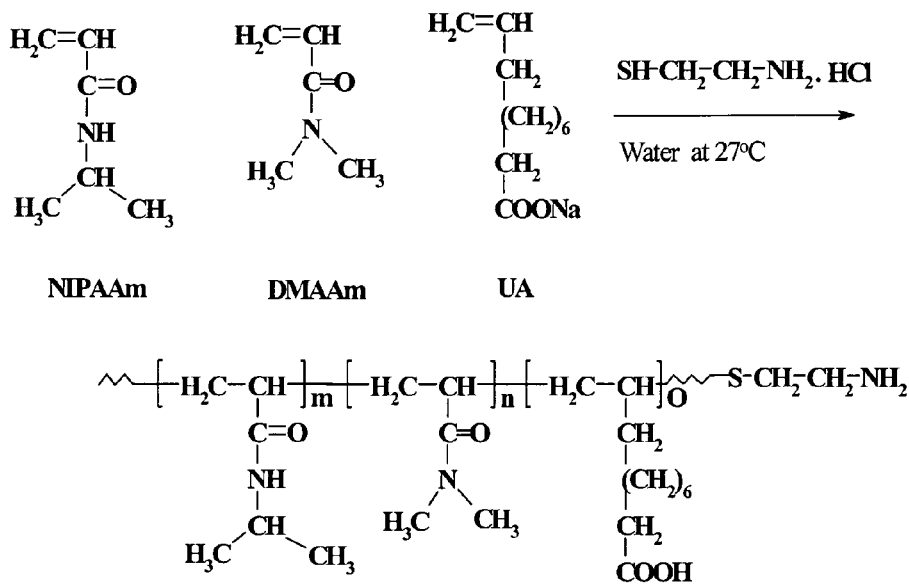
FIG. 1 shows Scheme 1, which illustrates one possible scheme for carrying out the synthesis of a copolymer of the invention, using the monomers N-isopropylacrylamide, N,N'-dimethylacrylamide and 10-undecenoic acid, and a chain transfer agent, aminoethanethiol, for illustrative purposes. Table 1 shows the various feed molar ratios used to form copolymers of the invention in exemplary experiments, and the physical characteristics of the resulting copolymers, namely, molecular weight, glass transition temperature, actual molar ratio of hydrophilic units to temperature-sensitive units, acidity, and the thermal degradation temperature. Aminoethanethiol was used as a chain transfer agent to introduce a terminating moiety into these copolymers.

The present invention is based on the finding that core-shell nanoparticles obtained from copolymers which incorporate fatty acids as hydrophobic, pH-sensitive functionalities possess excellent characteristics as drug carriers. The copolymers of the invention can self-assemble into a core-shell structure comprising a hydrophobic core, in which hydrophobic moieties such as the fatty acid are arranged, surrounded by a hydrophilic shell comprising hydrophilic moieties of the copolymer. Drugs can be encapsulated by either physical entrapment or chemical conjugation within the core. These nanoparticles are able to alter their physical configuration in response to a narrow window of change in environmental pH, resulting in the liberation of the drug encapsulated within the hydrophobic core of the nanoparticles.

One advantage of the copolymers of the invention is that the lower critical solution temperature (LCST) of core-shell nanoparticles formed from these copolymers can be made to be dependent on the environmental pH, meaning that structural deformation of the core-shell nanoparticles can be triggered by environmental pH changes. This property can be harnessed for use in targeting organs or tumour tissues where the environment is characteristically acidic. Under normal physiological pH, the core-shell nanoparticles have an LCST that is above normal body temperature (about 37° C.). However, in slightly acidic environments, the LCST of the nanoparticles is lower than the normal body temperature. This means that the core-shell nanoparticles are stable in the physiological environment but destabilise or aggregate in acidic environments.

Without wishing to be bound by theory, it is believed that the use of fatty acids as the hydrophobic, pH-sensitive portion of the copolymer helps to provide greater pH sensitivity in the copolymer of the invention. The pH sensitive functionalities are bound to hydrophobic segments of the fatty acid, meaning that they are assembled into the core of core-shell nanoparticles. It is also believed that core-shell nanoparticles made from these polymers are loosely packed, so that the pH sensitive functionalities remain accessible to the external environment despite being located at the core of the nanoparticles. When the pH of the external environment is changed, the pH sensitive functionalities can also be changed, e.g. ionised or deionised. This leads to changes to the hydrophobicity of the fatty acid, and thus alters the LCST of the nanoparticles, resulting in the release of drug molecules. Furthermore, as fatty acids are natural compounds, they are also believed to be highly biocompatible and should thus exhibit very low levels of toxicity within the human body.

The copolymer of the invention comprises at least three types of monomeric units. It is herewith mentioned for clarity that the term 'monomeric unit' refers to a monomer that has been polymerised into a polymer. It is distinguished from the term 'monomer', which denotes a distinct molecular entity which can be polymerised into a polymer.

One type of monomeric unit required in the copolymer of the invention is a temperature sensitive/responsive unit. In the present invention, temperature sensitive monomeric units are used to impart temperature sensitivity to the copolymers, resulting in the formation of temperature-sensitive copolymers. Temperature sensitive copolymers typically exhibit a distinct LCST or UCST (upper critical solution temperature), also known as phase transition temperature. Copolymers having a distinct LCST (hereinafter known as 'LCST systems') are insoluble in water above the LCST, while those having a distinct UCST are insoluble below the UCST. This characteristic is evidenced by conformational changes in the copolymer either when temperature change occurs across the critical solution temperature, or when the critical solution temperature of the copolymer shifts across a static environment temperature in response to pH changes, for example. In general, most drug delivery applications utilise LCST systems. The abrupt shrinking and the resulting insolubility of LCST systems when the environmental temperature is above the LCST allows the copolymer of the invention to leave the aqueous phase and assume a hydrophobic phase, thereby facilitating interaction with cell membranes. Furthermore, temperature sensitive monomeric units can be co-polymerized with hydrophilic co-monomers such as acrylamide (AAm), or other types of modifying co-monomers to achieve a higher or lower LCST. Such copolymers can be applied as a functional drug delivery material for controlling drug release rate.

Temperature sensitive monomeric units suitable for use in the invention may possess one or more polar functionalities, such as a primary, secondary or tertiary amino group, an amide group, a carboxyl group, a carbonyl group, or a hydroxyl group, all of which are polar by nature. Generally, due to the presence of polar functionalities, temperature sensitive monomeric units are consequently also hydrophilic in nature. Examples of temperature sensitive monomeric units that may be used in the invention include monomeric units derived from monomers such as substituted acrylamides, acrylates, pyrrolidone, piperidine, and cellulose. Specific examples of suitable temperature-sensitive monomeric units include, but are not limited to, those derived from N-isopropylacrylamide (NIPAAm), N-hydroxypropyl acrylate, N-acryloylpyrrolidone (APy), N-acryloylpiperidine, N-acroylpiperadine, hydroxy-methylcellulose, N-t-butylacrylamide, N-piperidyl-methacrylamide, for example. A presently preferred monomer that for used as the temperature sensitive monomeric unit of the invention is NIPAAm. Polymers incorporating monomeric units of NIPAAm are highly temperature sensitive, and display negative temperature sensitivity (i.e. LCST system), meaning that they become water soluble at temperatures falling below its LCST.

Another type of monomeric unit required in the present copolymer is a hydrophilic unit. In general, the hydrophilic monomeric unit provides a means to modify/shift the LCST of the copolymer of the invention. When the hydrophilic unit is relatively more hydrophilic than the temperature-sensitive hydrophilic unit, the LCST of the copolymer may be increased; conversely, if a relatively less hydrophilic unit or a hydrophobic unit is present, the LCST of the copolymer may be lowered. Hydrophilic monomeric units suitable in the invention include any suitable copolymerisable monomer, which may have one or more polar functionalities, such as a primary, secondary or tertiary amino group, an amide group, a sulfhydryl group, a carboxyl group, a carbonyl group, or a hydroxyl group. As opposed to the temperature sensitive monomeric unit in which polar functionalities may also be present and may thus also be hydrophilic in nature, hydrophilic monomeric units required in the invention do not have to be temperature-sensitive.

In certain embodiments, the hydrophilic monomeric unit is relatively more hydrophilic than the temperature sensitive hydrophilic unit. This serves to increase the LCST of the resulting copolymer. Hydrophilic monomeric units present in these embodiments may be derived from, but are not limited to, the following monomers: acrylic acid, acrylamide, acrylate, pyrrolidone, ethylene glycol and derivatives thereof. In specific embodiments, the hydrophilic monomeric unit can be derived from acrylamide and N-substituted acrylamide derivative monomers, including, but not limited to, acrylamide (AAm), N,N'-dimethylacrylamide (DMAAm), and N-(hydroxymethyl)acrylamide. In a preferred embodiment in which DMAAm is present in the copolymer of the invention, thermosensitivity was enhanced, thereby enabling 'on-off' drug release in response to smaller temperature changes in the body temperature. Additionally, with NIPAAm and DMAAm present in the copolymer of the invention, the LCST of the copolymer of the invention was raised (to a temperature slightly above 37° C.). It is generally desirable to utilise polymers in which the LCST of the copolymer is slightly above body temperature under physiological conditions. It is believed that no upper limit for the LCST is required, as long as the change in environmental pH from normal physiological pH (typically 7.4) to 7.2 or less is able to shift the LCST from a value higher than normal body temperature to a value lower than normal body temperature.

A third type of monomeric unit required in the copolymer of the invention is a hydrophobic unit derived from a copolymerisable unsaturated fatty acid and which comprises at least one pH-sensitive moiety. Any suitable unsaturated fatty acid which possesses at least one pH-sensitive functionality can be used in the invention. Suitable unsaturated fatty acids include all natural and artificially modified/synthesised fatty acids, and all monounsaturated and poly-unsaturated fatty acids having 1, 2, 3, 4, 5, 6, 7, 8 or more carbon-carbon double and/or triple bonds, as well as all cis- and trans-isomers thereof. The unsaturated portion of the fatty acid, i.e. the carbon-carbon double bond, may be present at any location in main carbon chain of the fatty acid.

The hydrocarbon chain of the unsaturated fatty acid constitutes the main hydrophobic portion of the copolymer. The hydrophobic portion is responsible for imparting hydrophobic nature to the copolymer of the invention. Hydrophobic portions are needed to form a core-shell structure and enable the copolymer to interact with other hydrophobic materials, such as anticancer drug molecules. The hydrocarbon chain of suitable fatty acids may be straight, unbranched alkyl chains typically found in natural fatty acids (including branched alkyl chains). It may also be cyclic or branched alkyl chains, optionally substituted with functional groups such as carboxylic acid, amine or hydroxyl groups, for example. No restriction is placed on the position of the functional groups. The carboxylic acid group provides, amongst other things, pH-sensitivity to the copolymer as well as the ability for conjugation with suitable ligands. Any other pH-sensitive functionality present in the fatty acid may also serve these functions.

In one embodiment, the copolymer of the invention has the following structural formula (I):

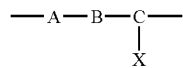

A, B and C, as defined in the above formula, depict the respective randomly co-polymerised monomeric units, namely, temperature-sensitive unit, hydrophilic unit and hydrophobic unit, or polymer blocks thereof. X denotes a carboxylic acid functional group which is directly bonded to the hydrophobic segment of the fatty acid.

In another embodiment, the unsaturated fatty acid comprises between (inclusive of) 5 to 50 or more main chain carbon atoms. In this embodiment, the fatty acid may comprise a single carbon-carbon double bond, meaning that it is a monounsaturated fatty acid. Specific monomers from which the hydrophobic monomeric unit can be derived include, for example, pentenoic, hexenoic, heptenoic, octenoic, nonenoic, decenoic, undecenoic, and dodecenoic acids. No specific restriction is placed on the position of the carbon-carbon double bond in the fatty acid.

Presently preferred mono-unsaturated fatty acids include, but is not limited to, fatty acids selected from the group consisting of (Z)-9-Tetradecenoic acid, (E)-9-Hexadecenoic acid, (Z)-9-Hexadecenoic acid, (E)-9-Octadecenoic acid, (Z)-9-Octadecenoic acid, (Z)-11-Octadecenoic acid, (Z)-11-Ecosenoic acid, (Z)-13-Docosenoic Acid and (Z)-15-Tetracosaenoic Acid.

In one embodiment, the monounsaturated fatty acid is an omega-1 fatty acid, meaning that the double bond is present between the first and second carbon atom at the end of the fatty acid that is opposite to the location of the carboxylic acid functional group. An advantage in using omega-1 fatty acids is that it enables the fatty acid to be readily copolymerised with the required temperatures-sensitive and hydrophilic monomeric units, as the carbon-carbon double bond is not sterically hindered by bulky alkyl chains. Presently preferred omega-1 fatty acids are selected from the group consisting of 4-pentenoic acid, 7-octenoic acid, 10-undecenoic acid, 15-hexadecenoic acid, and 19-ecosenoic acid.

In another embodiment, the fatty acid comprises at least 2 carbon-carbon double bonds, meaning that the fatty acid is polyunsaturated. Suitable polyunsaturated fatty acids include omega-3, omega-6 and omega-9 fatty acids as well as other types of fatty acids. Specific examples of polyunsaturated fatty acids which can be used in the invention include (E,E)-9,12-Octadecadienoic acid, (Z,Z)-9,12-Octadecadienoic acid, (E,E)-9,11-Octadecadienoic acid, (Z,Z,Z)-9,12,15-Octadecatrienoic acid, (Z,Z,Z)-6,9,12-Octadecatrienoic acid, (Z,Z,Z,Z)-6,9,12,15-Octadecatetraenoic acid, (Z,Z,)-11,14-Ecosadienoic acid, (Z,Z,Z)-5,8,11-Eicosatrienoic acid, (Z,Z,Z)-11,14,17-Eicosatrienoic acid, (Z,Z,Z)-8,11,14-Eicosatrienoic acid, (Z,Z,Z,Z)-8,11,14,17-Eicosatetraenoic acid, (Z,Z,Z,Z)-5,8,11,14-Eicosatetraenoic acid, (Z,Z,Z,Z,Z)-5,8,11,14,17-Eicosapentaenoic acid, (Z,Z)-13,16-Docosadienoic acid, (Z,Z,Z)-13,16,19-Docosatrienoic acid, (Z,Z,Z,Z)-7,10-13-16-Ocosatetraenoick acid, (Z,Z,Z,Z,Z)-4,7,10,13,16-Docosapentaenoic acid, (Z,Z,Z,Z,Z)-7,10,13,16,19-Docosapentaenoic acid, (Z,Z,Z,Z,Z,Z)-4,7,10,13,16,19-Docosahexaenoic acid, and (Z,Z,Z,Z,Z,Z)-6,9,12,15,18,21-Tetracosahexaenoic acid.

Copolymers of the present invention can comprise only the above-mentioned 3 types of monomeric units, or it may additionally include other types of monomeric units. For example, it is also possible to utilise two or more temperature-sensitive monomeric units, such as NIPAAm and N-t-butylacrylamide, or NIPAAm and N-piperidyl-methacrylamide. It is likewise possible to utilise two or more hydrophilic monomeric units, such as DMAAm and AAm, or DMAAm and APy. Other types of monomeric units can also be incorporated into the copolymer backbone to adjust the physicochemical properties of the copolymer, or introduce functional groups or spacers for further conjugation with ligands, these monomeric units including N-(hydroxymethyl)acrylamide or heterobifunctional PEG, for example.

Copolymers of the invention can be random copolymers in which the three main types of monomeric units, namely temperature-sensitive monomeric unit, hydrophilic monomeric unit and hydrophobic unit, are randomly distributed in the copolymer. It is also possible that the copolymer can be synthesised as a block copolymer such as a diblock or triblock block copolymer, as well as a block-graft copolymer. In one embodiment, the temperature-sensitive monomers and the hydrophilic monomers are copolymerised to form one block of polymers and the hydrophobic monomer is copolymerised to form another block of polymers, thereby forming a diblock copolymer.

In one embodiment, the copolymer further comprises at least one terminal group. The terminal group comprises at least one moiety selected from the group consisting of a terminating moiety, a ligand, a drug molecule, a tag, a radioimmunoconjugate, a moiety for modifying the physicochemical characteristics of the copolymer, and a spacer (linker).

In a specific embodiment, the copolymer of the invention comprises a terminal group that consists of a terminating moiety having the structure according to formula (II):

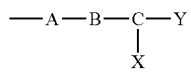

wherein Y is the terminating moiety.

In this embodiment, the terminal group is bonded to a terminal carbon atom in the carbon backbone (i.e. the carbon chain linking the monomeric units) of the copolymer. Typically, the terminating moiety can be introduced into the copolymer by adding a chain transfer agent containing the desired terminal structure to a mixture of reacting monomers, or it can be generated by living polymerisation methods. Chain transfer agents are able to stop the growth of a growing polymer chain by providing a 'quenching' atom to the active radical at the end of the growing chain. It in turn is left as a radical which can attack unreacted monomers and thus initiate the growth of a new chain. Accordingly, chain transfer agents can be used in the present invention to provide a suitable reactive functional group to a copolymer, as well as to obtain low molecular weight polymers. Examples of chain transfer agents include chloroform, carbon tetrachloride, aminoethanethiol, alkyl-mercaptans, octanethiol, decanethiol, n-dodecanethiol or t-dodecanethiol, mercapto-propionic acid, mercapto-succinic acid, thioglycolic acid, mercaptoethanol secondary alcohols thereof, alkyl halides, salts of phosphorus acids with an oxidation number less than 5, as well as other additives/chain limiters known to the skilled person. Other examples of chain transfer agents which can be used in the invention include solvents, impurities, or suitable modifiers.

In a further embodiment, the terminating moiety comprises at least one functional group selected from the group consisting of hydroxyl, carboxyl, carbonyl and amino functional groups. Amino functional groups are presently preferred, including primary or secondary amino groups. Amino groups can for example be present in an alkylthiol group that is bonded to the terminus of the copolymer, e.g. 2-amino-ethanethiol or 2,2-diamino-ethanethiol. The presence of amino groups in the terminating moiety allows modifications on the polymer and the targeting group to be made, for example, through the conjugation with ligands including, but not limited to, small targeting molecules (e.g. folic acid, other vitamins and acetylcholine etc.), proteins (e.g. transferrin and monoclonal/polyclonal antibodies etc.), peptides (e.g. TAT) and carbohydrates (e.g. galactose and polysaccharides), which may be recognised by specific receptors at desired cells, tissues or organs. In addition, the amino groups can also be conjugated with drugs or tags (e.g. fluorescent probes for visualization or purification of nanoparticles in a biological system of interest) or radioimmunoconjugates or chemical moieties to modify the polymer properties, for example attaching hydrophobic segments to increase hydrophobicity of the polymer.

It will be appreciated by the skilled person that the terminating moiety Y can be adapted to be a functional group that can react with functional groups present in ligands or tags or radioimmunoconjugates or drugs or other chemical moieties such as proteins. For example, where one or more carboxylic acid functional groups are present in the selected ligand, a terminating moiety having an amino group can be used for facilitating conjugation. Conversely, biological molecules that contain amino groups can be attached to a terminating moiety having a carboxylic acid functional group.

In order to provide a suitable functionality for biorecognition of a target receptor, the copolymer may be conjugated to one or more ligands capable of binding to functional groups present on the copolymer. Ligands which may be used include, but not limited to small targeting molecules, proteins, peptides and carbon hydrates.

In one embodiment, the terminal group consists of a terminating moiety and a ligand. Copolymers carrying ligands can be used to efficiently target a desired tissue in the body or specific types or compartments of cells. The targeting efficiency of the copolymer is enhanced by the pH sensitivity of the present copolymers.

Ligands which can be used in conjunction with copolymers of the present invention include, but are not limited to, small targeting molecules (e.g. folic acid, other vitamins and acetylcholine etc.), proteins (e.g. transferrin and monoclonal/polyclonal antibodies etc.), peptides (e.g. TAT) and carbon hydrates (e.g. galactose and polysaccharides). The number of biologically active ligands that can be present in a single copolymer can range from 1, 2, 3, 4, 5 or more in number.

Illustrative examples of growth factors (proteins and peptides) which are contemplated for use in the invention include Vascular Endothelial Growth Factor (VEGF), Epidermal Growth Factor (EGF), Platelet-Derived Growth Factor (PDGF), Fibroblast Growth Factors (FGFs), Transforming Growth Factors-b TGFs-b), Transforming Growth Factor-a (TGF-a), Erythropoietin (Epo), Insulin-Like Growth Factor-I (IGF-I), Insulin-Like Growth Factor-II (IGF-II), Interferon-g (INF-g), Colony Stimulating Factors (CSFS) are. Cytokines (proteins) that are contemplated for use include both lymphokines as well as monokines, and examples include Interleukin-1 (IL-1), Interleukin-2 (IL-2), Interleukin-6 (IL-6), Interleukin-8 (IL-8). If cancer is the disease to be treated, the selected ligand should preferably be recognised by a specific receptor on the cancer cells. Specific types of cancer cell receptor ligands that are contemplated for use with the copolymer of the invention include folic acid, targretin, alitretinoin, E. coli toxin, C3 cleavage fragments (C3d, C3dg and iC3b), Epstein-Barr virus gp350/220 and CD23 can be conjugated with the copolymers of the invention. Antibodies can also be used as cancer cell ligands, including monoclonal and polyclonal immunoglobulins obtained from mice, rabbits, chicken, goats and sheep and recombinant antibodies such as Fu fragments, scFu fragments, Fab fragments, or diabodies which are known to the skilled person. Cytokines that are contemplated for use include the TNF family of cytokines, including Tumour Necrosis Factor-a (TNF-a), Tumour Necrosis Factor-b (TNF-b), Fas Ligand (FasL) and TNF related apoptosis-inducing ligand (TRAIL). Other suitable ligands include transferrin, acetylcholine, biotin labels and folic acid. Prior modification of the ligand or of the copolymers of the invention (e.g. by incorporating functional groups that can react with complementary functional groups on the ligand) can be performed, if necessary.

In another embodiment, the terminal group is selected from the group consisting of a terminating moiety, a ligand, a tag, a drug molecule, a radioimmunoconjugate, or any other chemical moiety, e.g. a moiety for modifying the physico-chemical characteristics of the copolymer.

Copolymers incorporating a ligand, a drug, a tag, a radioimmunoconjugate or any other chemical moiety may have a general structure according to formula (III):

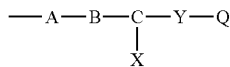

The terminating moiety Y can be bonded to a ligand, a tag, a drug, a radioimmunoconjugate, or a chemical moiety denoted by Q as shown in the above formula.

The ligands, tags, drug, radioimmunoconjugates, or chemical moieties are not limitedly bonded to the terminating moiety. In other embodiments, the ligands, tags, drugs, radioimmunoconjugates or chemical moieties may be coupled or conjugated to functional groups located on the temperature sensitive units or hydrophilic units. The terminal group may alternatively be bonded to any one of the monomeric units, such as a functional group in the hydrophilic unit or the temperature sensitive unit, instead of the terminating moiety Y. In such embodiments, the terminating moiety may or may not be present. This embodiment is shown in the following formula (IV) and (V):

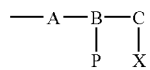 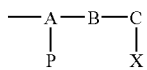

In this embodiment, P can be a ligand, a tag, a drug, a radioimmunoconjugate, or a chemical moiety.

In another embodiment, a hydrophobic molecule P', such as a drug molecule (e.g. doxorubicin) or a moiety for modifying the hydrophobicity of the copolymer, is conjugated to X. In so doing, the copolymer can be arranged into a core shell structure in which the hydrophobic molecule is located in the core (formula (VI)):

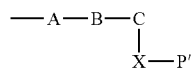

In the embodiments shown in the above formulas (III), (IV), (V) and (VI), a spacer -s- may optionally be positioned between the ligand or the tag or the radioimmunoconjugate or the drug or the chemical molecule and the terminating moiety (formula IIIs):

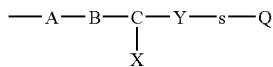

or optionally between B and P (see formula IVs):

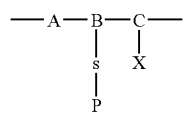

or optionally between A and P (see formula Vs):

or optionally be positioned between P' and the carboxyl group (see formula VIs):

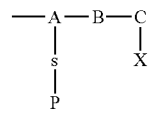

It is also possible for P, P' and Q, respectively, to be conjugated to both the terminating moiety (Y) and the functional groups of the hydrophilic monomeric units B, or B and X, or X and Y, or X and A, or Y and A, or A and B, or any three of A, B, X and Y in a single copolymer, as exemplified in the following formula (VII):

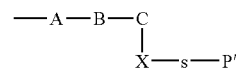

Each spacer -s- in the above formula (VII) can be the same or different.

The spacer can have any suitable length or number of main chain atoms, as long as the ligand or the tag or the radioimmunoconjugate is freely accessible to cells or tissues or organs after the self-assembly of the copolymers into the nanoparticles.

In preferred embodiments, one spacer is used, said spacer comprising more than 10 main chain atoms. An example of such a spacer can, for example, be derived from polyoxyalkylene compounds such as poly(ethylene glycol) and poly(propylene glycol). The ligand or the tag or the radioimmunoconjugate can be present at any position on the spacer molecule. In one embodiment, the ligand or the tag or the radioimmunoconjugate is bonded to functional groups positioned at a terminal main chain atom of the spacer molecule. In other embodiments, the ligand or the tag or the radioimmunoconjugate is bonded to functional groups located in any one of the side chains, of the spacer molecule, if present.

Copolymers of the present invention can be advantageously employed as a material for drug delivery, especially for the delivery of drugs which are hydrophobic in nature. As the copolymers are amphiphilic in nature and as the water solubility of the copolymer can be manipulated by temperature and/or pH changes, hydrophobic drugs can be conveniently packaged in a core-shell structure, typically known as a core-shell nanoparticle, using the present copolymers. When the composition of the invention is prepared in the aqueous phase below the LCST of the copolymer, the copolymer and the hydrophobic drug will self-assemble into a core-shell arrangement, whereby the hydrophobic drug is positioned in the core, where it will interact with the hydrophobic segments of fatty acid monomeric units. The temperature-sensitive and hydrophilic monomeric units will be positioned in the shell, interacting with the solvent (water) molecules or other polar molecules and thereby rendering the hydrophobic drug soluble in the aqueous phase. In this way, hydrophobic drugs can be rendered water soluble and can be transported in the blood stream. Since there are carboxylic acid groups present in the hydrophobic segments (i.e. fatty acid units), hydrophilic drugs, proteins or peptides can also be encapsulated within the core of the nanoparticles, protecting the enclosed drugs, proteins and peptides against degradation and enabling them to exhibit prolonged activity in the systemic circulation by avoiding the scavenging of the reticuloendothelial systems (RES). When the drug is packaged in a core-shell nanoparticle, it forms a composition, which can be readily administered to a patient, either intravenously, orally, intramuscularly, topically, or through the ocular route or inhalation. In general, there is no restriction to the molecular weight of the copolymer that is used to form the nanoparticle. However, it is preferable to keep the molecular weight of the copolymer to less than 40,000 in order for the polymer to be excreted through the kidney. Several parameters may influence the size of nanoparticles formed using the present copolymer, including polymer concentration, drug loading level and fabrication conditions of the nanoparticles. The size of nanoparticles synthesised from copolymers disclosed herein may typically be less than 200 nm, particularly for enhanced permeability and retention (EPR) effect and long circulation in plasma.

Each of the at least three monomeric units can be present in copolymers of the invention in any suitable ratio. In general, the ratio of monomeric units can be varied to achieve desired LCST and pH characteristics. The ratio also depends on other factors such as the type and number of functional groups present in each monomeric unit and the pH- and temperature-sensitivity of the copolymer. The molar ratio of monomeric units present in the copolymer largely depends on the feed molar ratio of each monomeric unit used to prepare the copolymer.

In one embodiment, the molar quantity of temperature-sensitive monomeric unit present in the copolymer of the invention is larger than that of the hydrophilic monomeric unit to avoid dilution effect of the hydrophilic unit on the temperature-sensitivity of the final copolymer; the molar quantity of hydrophilic monomeric unit is in turn is larger than the amount of hydrophobic monomeric unit in the copolymer. In certain embodiments, the feed molar quantity of temperature-sensitive monomers used to prepare copolymers of the invention is between about 2 to 6 times more than the feed molar quantity of hydrophilic monomers, and between about 4 to 8 times more than the feed molar quantity of hydrophobic monomers. Examples of feed molar ratios that can be used to form useful copolymers are 1 to 4 molar ratio of temperature sensitive monomer; 0.5 to 1.5 molar ratio of hydrophilic monomer; 0.01 to 0.75 molar ratio of hydrophobic monomer. In a particularly suitable embodiment, the respective monomers that were used according to this range of feed molar ratios are N-isopropylacrylamide, N,N'-dimethylacrylamide and 10-undecenoic acid.

In one preferred embodiment, the LCST of the core-shell nanoparticles is less than 37° C. at a pH of less than 7, or preferably less than 7.2. In another embodiment, the lower critical solution temperature of the core-shell nanoparticles is higher than 37° C. under the normal physiological conditions (pH 7.4). It is noted that the LCST of the copolymer can be controlled, either raised or lowered, by varying the percentages of monomeric units or the nature of hydrophilic monomeric units used to form the copolymer. It is presently preferred to have a copolymer in which the LCST of the core-shell nanoparticles at a physiological pH is above the normal body temperature, i.e. 37° C., and the LCST is below the normal body temperature in an acidic environment. Reversible, pH-dependent LCST and phase transition characteristics are displayed by nanoparticles formed using copolymers of the present invention. For example, in one specific experimental set up, in which core-shell nanoparticles were self-assembled in aqueous solutions from the copolymer of N-isopropylacrylamide, N,N'-dimethylacrylamide and 10-undecenoic acid in a mole ratio of 3.75:1.25: 0.5, the LCST of the core-shell nanoparticles formed at this specific composition was 38.5° C. in phosphate-buffered saline (PBS, pH 7.4), which decreased significantly (35.5° C.) in a slightly acidic environment (e.g. less than pH 6.6).

Drugs which have been contemplated for use in the invention include, but are not limited to, anti-cancer drugs, anti-inflammatory drugs, drugs for treating nervous system disorders, and immunosuppressants etc. For example, doxorubicin, anastrozole, exemestane, cyclophosphamide, epirubicin, toremifene, letrozole, trastuzumab, megestrol, nolvadex, paclitaxel, docetaxel, capecitabine, goserelin acetate, cyclosporin, cisplatin, indomethacin, betamethason and doxycycline.

For efficient drug delivery, it is advantageous for the drug carrier to promote lesion targeting and intracellular access. Targeting, and subsequent internalization under certain conditions of the drug carriers may be achieved by coupling the drug carrier with a normally endocytosed ligand, taking advantage of the natural endocytosis pathway. Using this strategy, copolymers of the invention can be incorporated with a variety of ligands, such as monoclonal antibodies, growth factors, or cytokines, can be used to facilitate the uptake of carriers into target cells. Small and non-antigenic ligands are presently contemplated for use in the invention in order to avoid difficulties in diffusion through biological barriers, e.g. cell walls of the target cell, as well as immunogenecity.

In one embodiment, folic acid is used as the ligand. Folic acid (MW=441 Da) is a low molecular weight and non-antigenic ligand, good as a targeting signal of tumour cells. Folic acid is a vitamin whose receptor is frequently expressed on the surface of the human cancer cells. Additionally, it exhibits very high affinity for its cell surface receptor (Kd ~10-10 M) and it can move into cytoplasm. Folic acid has been found to follow the caveolae-mediated endocytosis, rather than end up in lysosomes, where the contents are rapidly degraded. Thus, by using folic acid as a ligand in drug compositions using copolymers disclosed herein, drugs can be delivered to a desired intracellular locality, safe from degradative enzymes. It is also known that endosomes reachable via the caveolae pathway are also acidic. Due to their acidity, endosomes can alter the LCST of nanoparticles (from a temperature higher than body temperature to a temperature lower than body temperature), breaking down the endosome membrane. Therefore, intracellular drug delivery into the cytoplasm can be achieved.

It is to be noted that the compositions to which invention is directed is not limited to core-shell structured nanoparticles in which the therapeutic drug is loaded into the hydrophobic core of the nanoparticles via hydrophobic interaction with the hydrophobic moieties in the copolymer. It is possible to covalently bond molecules of the therapeutic drug to the copolymer by reacting the drug molecule to suitable functional groups located on any part of the copolymer, such as by reacting the carboxyl groups on fatty acids with amino groups or hydroxyl groups on the drug molecule, for example. Compositions in which the drug molecule is conjugated with the copolymer may assume both core-shell structures or micellar structures or any other stable structure suitable for facilitating drug delivery. The conjugation of drugs to the copolymer of the invention provides an alternative but similarly effective means of delivering drugs to a target organ/cell location.

Figure 23:
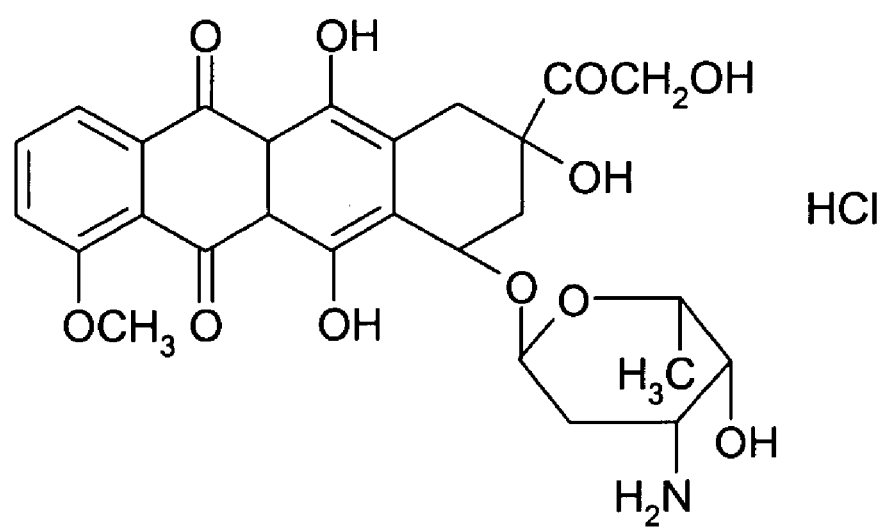
FIG. 23 shows the structural formula of doxorubicin hydrochloride.
Figure 24:
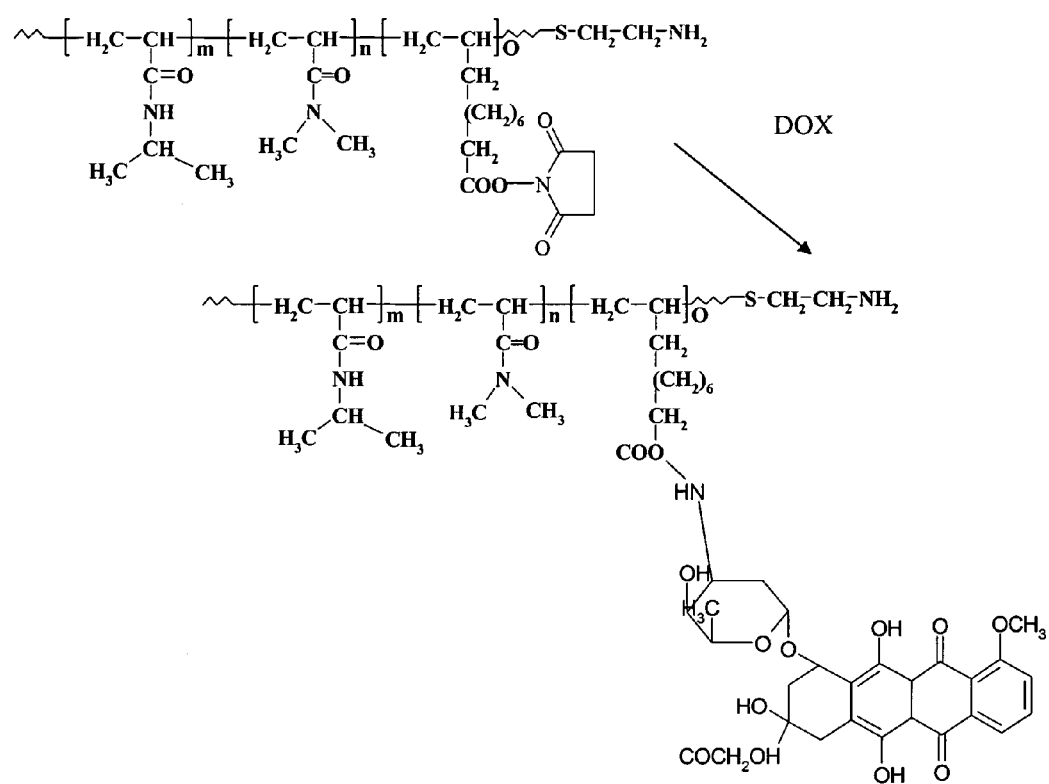
FIG. 24 shows the synthesis of doxorubicin conjugated Polymer II.

In another embodiment in which doxorubicin is used as the therapeutic drug in a composition of the invention, doxorubicin was conjugated to the copolymer through carbodiimide chemistry. The amine functional group of doxorubicin was conjugated to carboxyl functional groups of a copolymer of the invention, as presented in FIGS. 23 and 24.

The following examples are offered in order to more fully illustrate the invention, but are not to be construed as limiting the scope thereof.

EXAMPLE 1

Synthesis of poly(N-isopropylacrylamide-co-N,N-dimethylacrylamide-co-10-undecenoic acid) [P(NIPAAm-co-DMAAm-co-UA)]

A) Experimental Section i) Materials

Unless stated otherwise, all reagents and solvents were of commercial grade, and were used as received. N-isopropylacrylamide, N,N-dimethylacrylamide and 10-undecenoic acid (98%) were purchased from Aldrich, and were purified by crystallization (n-hexane) and reduced-pressure distillation, respectively. The chain transfer agent (CTA), 2-aminoethanethiol hydrochloride (AET.HCl), was purchased from Sigma, Aldrich. Trinitrobenzene sulfonate (TNBS) 1 M aqueous solution was purchased from Fluka. Doxorubicin hydrochloride was kindly provided by Sun Pharmaceuticals, India. 3-[4,5-Dimethylthiazolyl-2]-2,5-diphenyl tetrazolium bromide (MTT, Duchefa) was used in a 5 mg/mL PBS (pH 7.4) solution for cell quantification. The solution was filtered with a 0.22 μm filter to remove blue formazan crystals.

ii) Synthesis

P(NIPAAm-co-DMAAm-co-UA) polymers with various compositions were synthesized by the radical copolymerization using the redox couple ammonium persulfate (APS) and 2-aminoethanethiol hydrochloride (AET.HCl) (FIG. 1) [Bokias et al. Macromol. Chem. Phys. 199 (1998) 1387-1392]. The polymerization procedure is briefly explained as follows. N-isopropylacrylamide (3.965 g, 34.99 mmol) and N, N-dimethylacrylamide (1.48 g, 14.99 mmol) were dissolved in 10 mL of ultra pure water. Undecenoic acid (0.921 g, 5.0 mmol) was converted into sodium salt by reacting with 5 mL of 4% sodium hydroxide solution, and the clear solution of sodium salt was added to the N-isopropylacrylamide and N,N-dimethylacrylamide solution. The mixture was purged with purified nitrogen gas for 15 minutes. APS (0.254 g, 4.0 mol % of the monomer feed) and AET.HCl (0.244 g, 2.16 mmol, 4.0 mol % of the monomer feed) were dissolved in 5.0 mL of ultra pure water. The solution was added to the monomer solution slowly with continuous stirring. The reaction was carried out under nitrogen at 27° C. for 48 hours. Upon completion, the crude product was precipitated by the addition of excess sodium chloride and dried under vacuum. The crude product was dissolved in ethanol, and was dialyzed against ultra pure water followed by ethanol using a membrane with a molecular weight cut-off of 2000 (Spectra/Por). The purified product was collected after evaporating ethanol.

The chemical structure of the polymers was characterized by $^1$H NMR (Bruker AVANCE 400) and Fourier transform infrared (Perkin Elmer Spectrum 2000, KBr) spectroscopic methods. The molecular weights of polymers were determined by gel permeation chromatography (GPC, Waters, polystyrene standards) in THF (elution rate: 1 mL/min) at 25° C. Differential scanning calorimetry (DSC) experiments were performed using a TA 2920 Modulated DSC instrument (CT, USA) with a ramp speed of 3° C./min. Thermogravimetric analyses were performed using TGA 7 (Perkin Elmer, USA).

iii) Acid-Base Titration and Amine Group Determination

Acid-base titration was performed to estimate carboxylic acid groups and pKa of the polymer. Briefly, 100 mg of polymer was dissolved in 10 mL of ultra pure water and titrated with 0.01N NaOH using phenolphthalein as an indicator. The apparent partition coefficient pKa of the polymer was also determined by this titration method with continuously measuring pH during the addition of base. From the graph of pH versus the volume of base, pKa was calculated as the pH at half the volume of the base at the equivalence point. The free amine group in the polymer was estimated by spectroscopic determination. A known amount of polymer was dissolved in 2.0 mL of sodium hydrogen carbonate aqueous solution (2.0 w/v %) containing 0.01M TNBS. The solution was kept for 2 hours at 40° C., which was then cooled and diluted to a specific volume. The amount of amine functional groupes derivatized with TNBS in the sample was determined by using a UV-VIS spectrophotometer (UV-2501PC, Shimadzu) at 345 nm taking L-alanine as standard.

iv) Transmittance Measurements

The LCSTs of polymers in buffer solutions of different pH values were determined by monitoring the optical transmittance change as a function of temperature. Sample solutions (0.5 wt %) were prepared in buffers such as neutralized phthalate buffer (pH 5.0), PBS (pH 6.0, 6.6 and 7.4), as well as in alkaline borate buffers with pH 9.0 and 10.0. All the buffers were prepared with an ionic strength of 154 mM. Optical transmittance of the polymer solutions was measured at 500 nm with the UV-VIS spectrometer with the sample cell thermostated using a temperature-controller (TCC-240A, Shimadzu). The heating rate was set at 0.1° C./min. The LCST values of polymer solutions were determined at the temperatures showing an optical transmission of 50%. The effect of proteins on the LCST was also investigated in the presence of 10 (w/v) % bovine serum albumin (BSA, as a model protein).

v) Fluorescence Measurements

The CMC values of the polymer in PBS (pH 7.4) were determined by fluorescence spectroscopy using pyrene as a probe. Aliquots of pyrene solutions ($1.54 \times 10^{-5}$ M in acetone, 400 μl) were added to 10 mL volumetric flasks, and the acetone was allowed to evaporate. Polymer solutions at concentrations ranging from $1.0 \times 10^{-5}$ to 1.0 g/L were prepared in PBS. 10 mL of the aqueous polymer solutions were then added to the volumetric flasks containing the pyrene residue. It should be noted that all the sample solutions contained excess pyrene content at the same concentration of $6.16 \times 10^{-7}$ M. The solutions were allowed to equilibrate for 24 hours at room temperature (20° C.). Fluorescence spectra of the polymer solutions were then recorded on a LS50B luminescence spectrometer (Perkin Elmer, USA) at room temperature. The emission spectra were recorded from 350 to 500 nm with an excitation wavelength of 340 nm. Both excitation and emission bandwidths were set at 5 nm. From the pyrene emission spectra, the intensity (peak height) ratio ($I_3/I_1$) of the third band (391 nm, $I_3$) to the first band (371 nm, $I_1$) was analyzed as a function of polymer concentration. The CMC value was taken from the intersection of the tangent to the curve at the inflection with the horizontal tangent through the points at low concentrations.

vi) Preparation of Blank and Drug-Loaded Core-Shell Nanoparticles

The blank core-shell nanoparticles were prepared to investigate the effect of pH and temperature on the size of the nanoparticles. The polymer was dissolved in dimethylacetamide (DMAc) at a concentration of 0.5 (w/v) %, which was then dialyzed against 0.02 wt % HCl, and 0.02 wt % NaOH for 24 hours using a membrane with a molecular weight cut-off of 2000 (Spectra/Por) at room temperature, respectively. The resultant nanoparticle solutions were freeze-dried after being filtered with a 0.45 μm syringe filter and stored at 4.0° C. prior to further analyses. DOX was loaded in the core-shell nanoparticles using a similar protocol as reported by F. Kohori et al. [supra]. Briefly, 7.5 mg of DOX was neutralized with two moles excess triethylamine in 3 mL of DMAc and the solution was stirred to dissolve the drug. 15 mg of polymer was then dissolved in the solution. The mixture was dialyzed against 500 mL of de-ionized water for 48 hours. The DOX-loaded nanoparticles were filtered and freeze-dried. To determine DOX loading level, a known amount of DOX-loaded nanoparticles was dissolved in 1 mL of methanol and then diluted with PBS. The DOX concentration was estimated by using the UV-VIS spectrophotometer at 485 nm. The drug loading was calculated based on the standard curve obtained from DOX in PBS (pH 7.4).

vii) Dynamic Light Scattering (DLS) Analyses

The size of the core-shell nanoparticles fabricated at different pH was analyzed using ZetaPals (Brookhaven instruments corporations, CA, USA) equipped with a He—Ne laser beam (670 nm). Each measurement was repeated five times, and was found to be in a good agreement. An average value was obtained from the five measurements. The size of the nanoparticles was also measured at various temperatures to study the phase reversibility of the nanoparticles. The stability of the re-dispersed freeze-dried nanoparticles was monitored by measuring their size in PBS (pH 7.4) containing 10 (w/v) % bovine serum albumin (BSA).

viii) Transmission Electron Microscopy (TEM) Examinations

The morphology of the core-shell nanoparticles was analyzed by TEM. A drop of the freshly prepared nanoparticle solution containing 0.01 (w/v) % phosphotungstic acid was placed on a copper grid coated with a polymer film, and was air-dried at room temperature. The TEM observations were carried out on a JEM-2010 microscope with an electron kinetic energy of 200 k eV.

ix) Cytotoxicity Study

Polymer solutions were prepared at stock concentrations. These solutions were sterilized with 0.22 μm syringe filters and diluted with PBS (pH 7.4) and growth media to give the polymer at final concentrations of 10, 100, 300 and 400 μg mL$^{-1}$. Poly(L-lysine) and PEG (Mw 8,000) at a concentration of 33.3 μg mL$^{-1}$ were used as the positive and negative controls, respectively. PBS (pH 7.4) was used for the blank sample instead.

The L929 mouse fibroblast cells were cultured in supplemented Dulbecco's Modified Eagle's Medium (DMEM, 10% fetal bovine serum, 1% L-glutamate, 1% penicillin-streptomycin) (GibcoBRL) and incubated at 37° C., 5% $CO_2$. The cells were seeded onto 96-well plates at 10,000 cells per well. The plates were then returned to the incubator and the cells were allowed to grow to confluence. On the morning of the initiation of the tests, the media in the wells were replaced with 150 μl of the pre-prepared growth medium-sample mixture. The plates were then returned to the incubator and maintained in 5% $CO_2$, at 37° C., for 24, 48 and 72 hours. The mixture in each well was replaced with fresh aliquots every morning for the exposure period. Each sample was tested in eight replicates per plate. Three plates were used for each period of exposure, making a total of 24 replicates per sample.

Fresh growth media and 20 μL aliquots of MTT solution were used to replace the mixture in each well after the designated period of exposure. The plates were then returned to the incubator and maintained in 5% $CO_2$, at 37° C., for a further 3 hours. The growth medium and excess MTT in each well were then removed. 150 μl of DMSO was then added to each well to dissolve the internalised purple formazan crystals. An aliquot of 100 μL was taken from each well and transferred to a fresh 96-well plate. The plates were then assayed at 550 nm and 690 nm. The absorbance readings of the formazan crystals were taken to be that at 550 nm subtracted by that at 690 nm. The results were expressed as a percentage of the absorbance of the blank, which comprised PBS of a comparative volume, added to the growth medium.

x) In Vitro Drug Release Studies

DOX release from the nanoparticles was studied at pH 6.0, 6.6 and 7.4. A certain amount of DOX-loaded freeze-dried nanoparticles was dispersed in 200 μL of the respective buffer solution and allowed to stabilize for 30 minutes before being placed in a dialysis membrane with a molecular weight cut-off of 2000 (Spectra/Por). The dialysis bag was then immersed in 25 mL of PBS with pH 6.0, 6.6 or 7.4 at 37° C. The samples were drawn at specific time intervals and the drug concentration was analyzed using the UV-VIS spectrophotometer as stated in paragraph A(vi) of the present example.

B) Results and Discussion i) Polymer Synthesis and Characterization.

A summary on the synthesis and characterization of the copolymers is given in Table 1. In these reactions, the feed molar ratios of NIPAAm to DMAAm varied but the content of 10-undecenoic acid was fixed. The CTA was used at 0.2 and 0.4 mol % of the monomer feed. The polymerization was initiated by the thiol redicals, created from the reaction of AET.HCl with persulphate ions, according to the following equation:

$$2RSH + S_2O_8^{-2} \longrightarrow 2RS^{-} + 2HSO_4^{-}$$

where R represents the aminoethyl group. Furthermore the thiol groups are known to be effective chain transfer agents [Greeg et al., J. Am. Chem. Soc. 70 (1948) 3740-3743]. Thus in this case, the length of the produced chain is controlled by the molar ratio of the AET.HCl to the monomer feed and the efficiency to initiate polymerization and to do chain transfer reaction. This initiation mechanism by the thiol radical in redox systems is well established [Khune et al., Polym. Prpr. 22 (1981) 76-77]. In addition, for our polymers prepared with this initiator couple, the average number of amine functional groups in each polymer molecule was estimated to be 1.3 to 1.7. The results were slightly over estimated probably due to the fact that the average molecular weight of polymer was taken for the calculation. A further more decrease in the pH of the reaction medium was observed, which indicates the production of acidic $HSO_4^-$. The molecular weights determined by GPC indicate that an increased CTA content yielded a decrease in molecular weight, which was in agreement with the results reported by G. Bokias et al. [supra].

Figure 2:
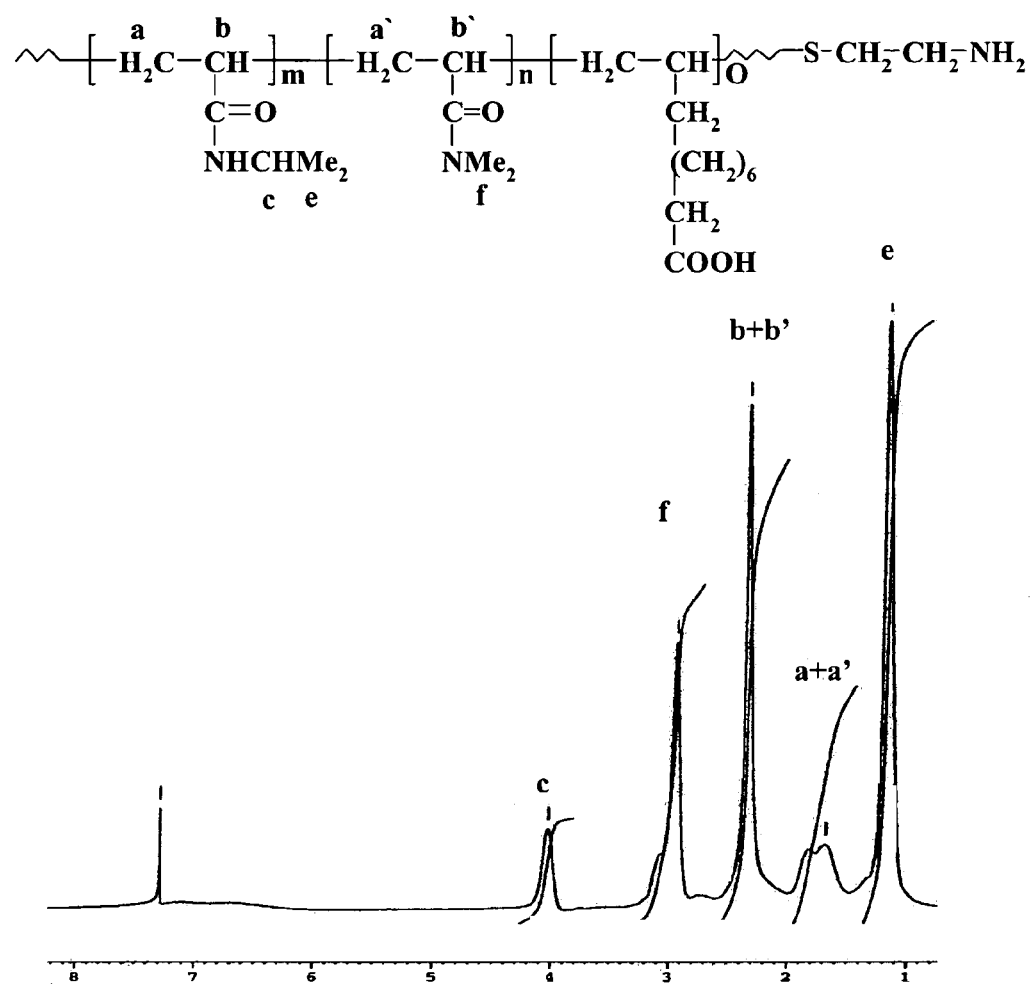
FIG. 2 depicts a typical $^1$H NMR spectrum of a polymer obtained from monomers N-isopropylacrylamide, N,N'-dimethylacrylamide and 10-undecenoic acid synthesised from a feed molar ratio of 3.5:1.5:0.5 (Polymer III) in CDCl$_3$.
Figure 3:
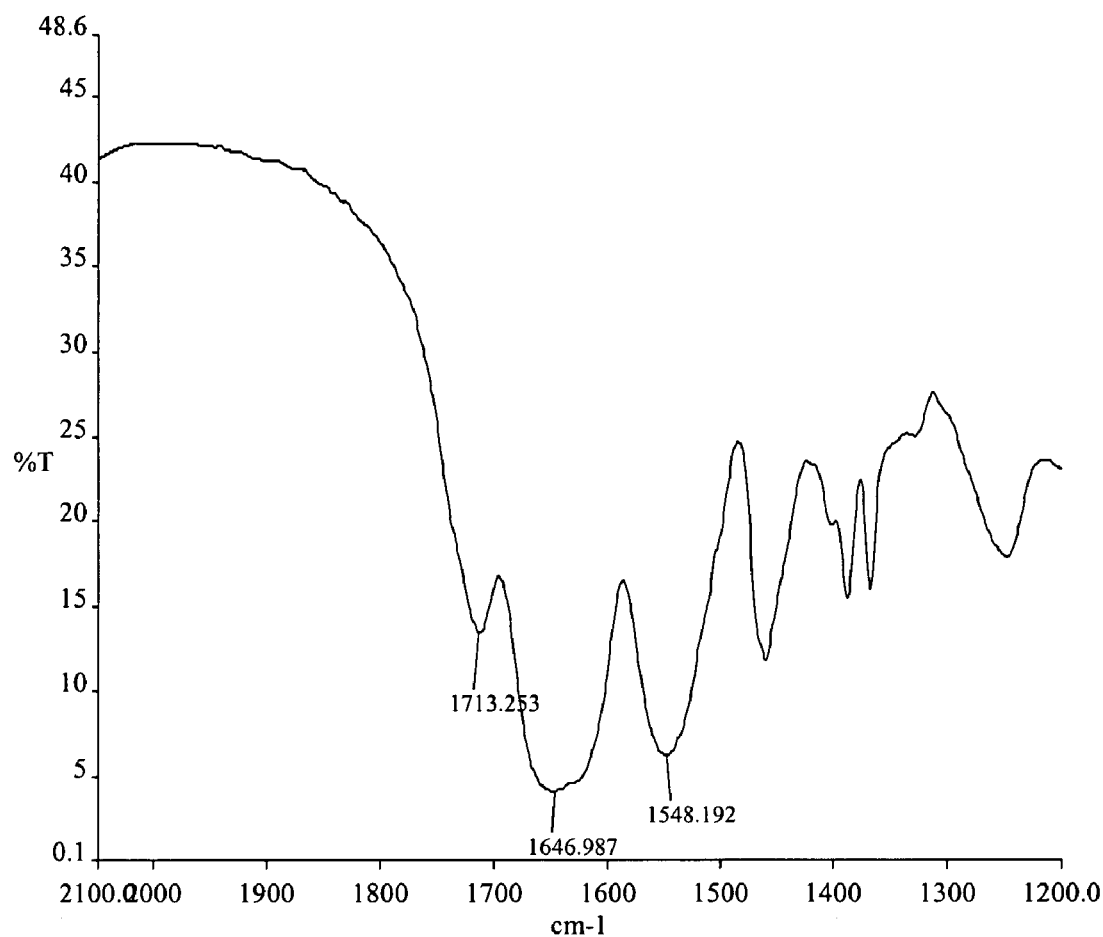
FIG. 3 depicts a typical FT-IR spectrum of Polymer III.

The $^1$H NMR spectra of all the three polymers shared a similar pattern. A typical $^1$H NMR spectrum of Polymer III (NIPAAm:DMAAm:UA=3.50:1.50:0.50) in $CDCl_3$ is shown in FIG. 2. The success of the copolymerization of NIPAAm, DMAAm and 10-undecenoic acid in the presence of the chain transfer agent was evidenced by the absence of vinylic proton signals at δ 5.4-6.6. The broad peaks at δ 1.5-1.8 (Signal a+a') and at δ 2.1-2.4 (Signal b+b') were attributed to the protons of —$CH_2$— and —CH— groups in the NIPAAm and DMAAm moieties, respectively. Other proton signals from iso-propyl groups (—$CHMe_2$ at δ 4.0 and —$CHMe_2$ at δ 1.15, Signals d and e, respectively) and —$NMe_2$ groups at δ 2.9 (Signal f) were also observed, and their chemical shifts were similar to those of the monomers. From the integration ratio of Signal e to Signal f, the m/n ratio was estimated, which was approximately equal to the feed ratio of the two monomers. This means that the two monomers had similar reactivity in the polymerization reactions. The FT-IR spectrum of Polymer II is shown in FIG. 3. It exhibited strong absorptions at about 1647 $cm^{-1}$ ($v_{C=O}$) and 1548 $cm^{-1}$ ($v_{C-N}$) from NIPAAm and DMAAm segments. The absorption of $v_{C=O}$ in the 10-undecenoic acid segments appeared at about 1713 $cm^{-1}$. The content of UA was estimated as 44.2 mg/g Polymer II by the acid-base titration analyses (Table 1). The pKa of Polymer II was about 6.8. The polymers exhibited good solubility in both water and common organic solvents ($CHCl_3$, $CH_2Cl_2$, acetone and THF etc.).

ii) LCST of Polymers and the Effects of pH and Proteins

Figure 4:
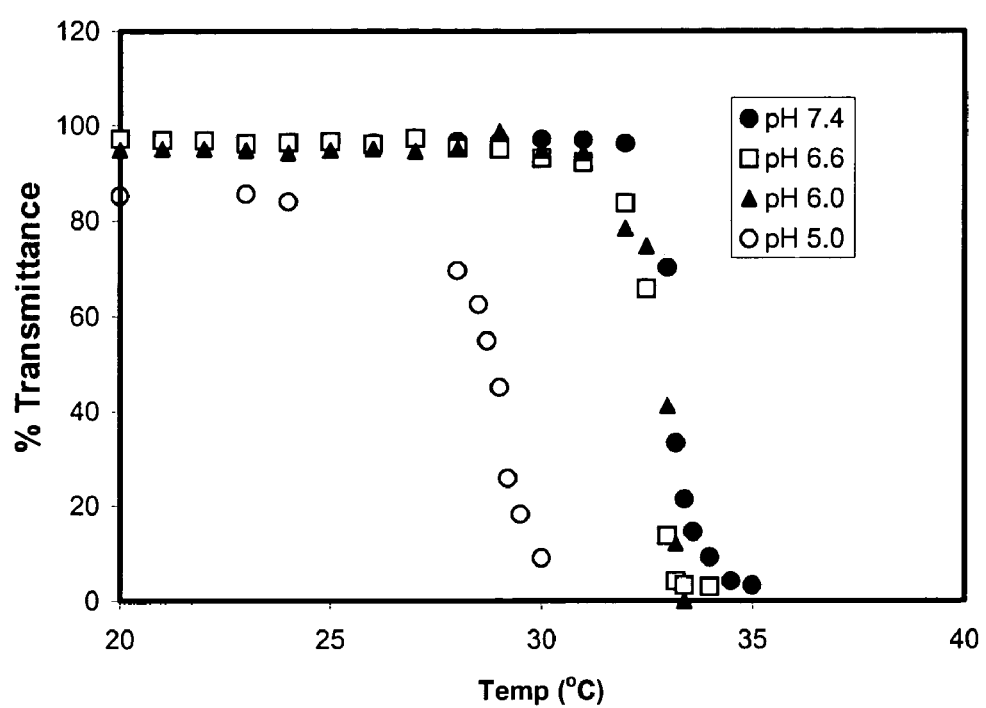
FIG. 4 depicts a plot of optical transmittance of the polymer obtained from monomers N-isopropylacrylamide, N,N'-dimethylacrylamide and 10-undecenoic acid synthesised from a feed molar ratio of 4.0:1.00:0.5 (Polymer I) as a function of temperature at varying pH at 500 nm.
Figure 5:
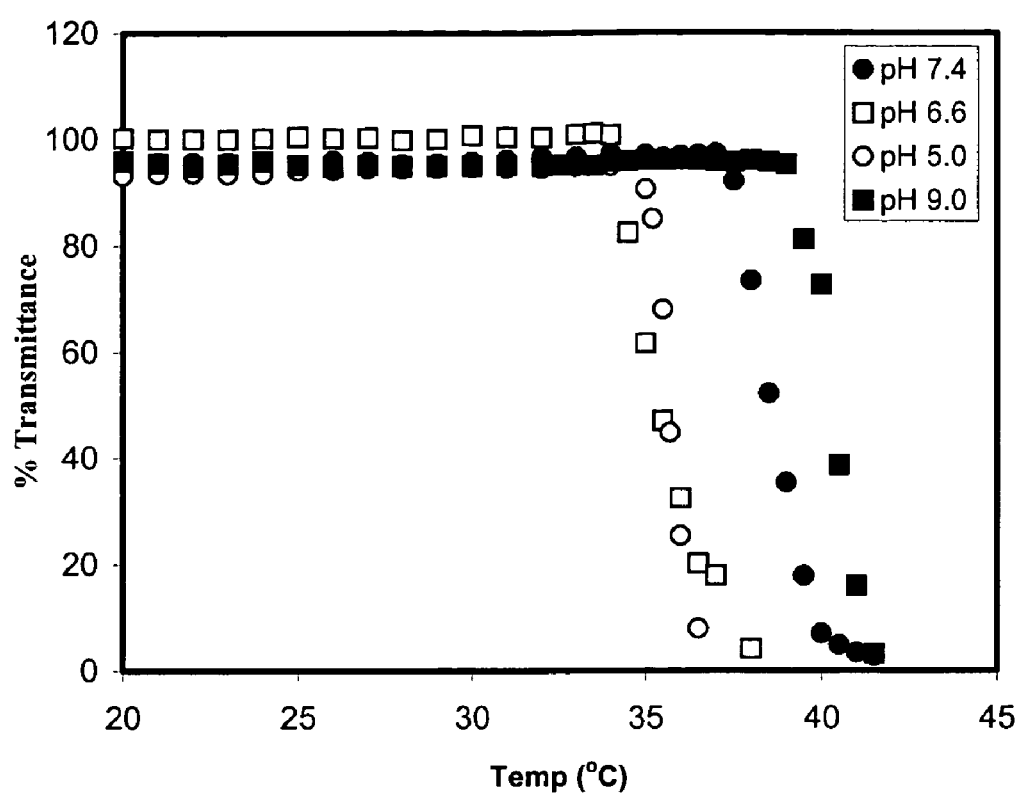
FIG. 5 depicts a plot of transmittance of the polymer obtained from monomers N-isopropylacrylamide, N,N'-dimethylacrylamide and 10-undecenoic acid at a molar ratio 3.75:1.25:0.5 (Polymer II) as a function of temperature at varying pH at 500 nm.
Figure 6:
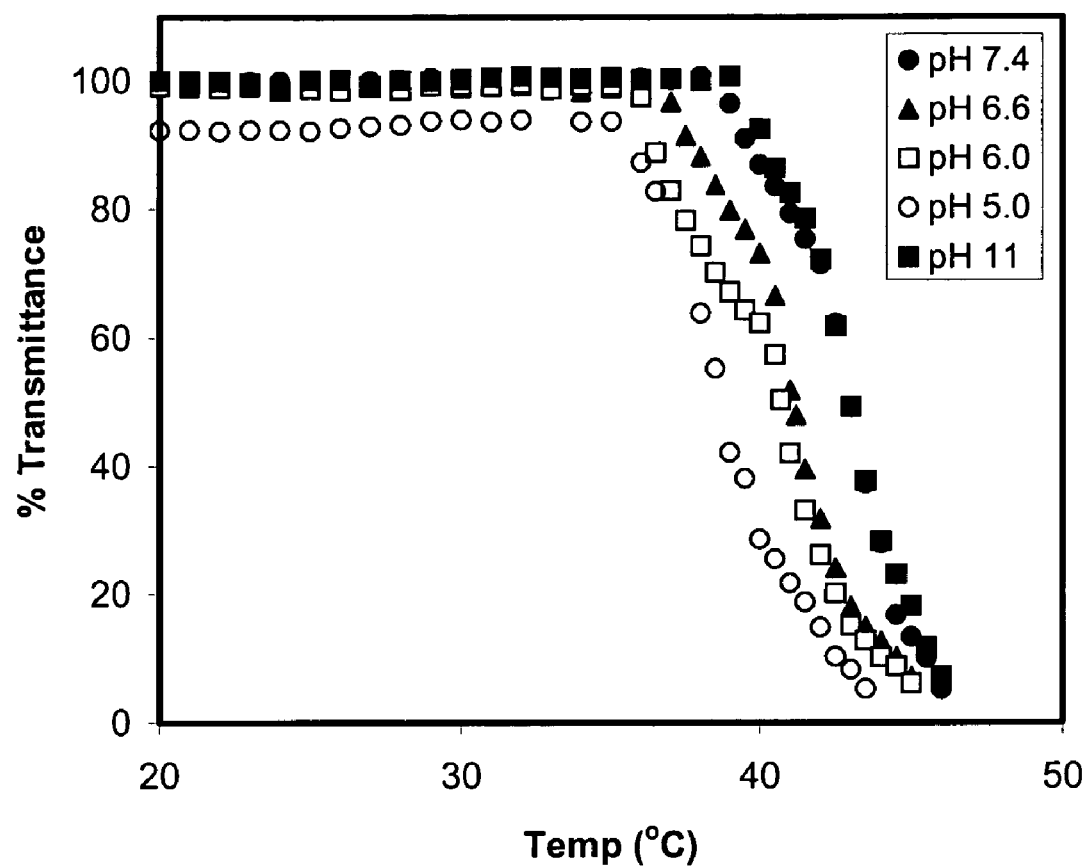
FIG. 6 depicts a plot of transmittance of Polymer III as a function of temperature at varying pH at 500 nm.

PNIPAAm exhibits a well-defined LCST of 32° C. in water. The LCST can be modulated via introducing hydrophobic or hydrophilic monomers. The polymers synthesized in this study contains poly(10-undecenoic acid) as the hydrophobic segment. Thus, environmental pH could influence the hydrophobicity of the 10-undecenoic acid segment through the carboxylic acid groups, which could finally affect the LCST of the polymers. FIGS. 4 to 6 show the optical transmittance changes of the polymers at a concentration of 0.5 wt % in buffer solutions of various pH values as a function of temperature. From the DLS analyses, the polymers in the buffer solutions self-assembled into core-shell nanoparticles at the concentration of 0.5 wt %. The LCST of the core-shell nanoparticles self-assembled from Polymer I with the NIPAAm/DMAAm/UA ratio of 4.00: 1.00:0.5 at pH 6.0, 6.6 and 7.4 was 32.5, 33.0 and 33.2° C., respectively (FIG. 4). However, at pH 5.0, the LCST was drastically reduced to 27.8° C. In the case of polymer II with an increased length of the hydrophilic DMMm segment (NIPAAm:DMAAm:UA=3.75:1.25:0.5), the LCST of the core-shell nanoparticles at all the pH values was increased (FIG. 5) when compared to polymer I. The pH value had a significant effect on the LCST of Polymer II nanoparticles. For instance, at pH 9.0 and 7.4, the LCST was found to be 40.5 and 38.5° C., respectively, which were well above the normal body temperature. However, at pH 6.6 and 5.0, the LCST was reduced to 35.5 and 35.2° C., respectively, which were much lower than the normal body temperature. If the nanoparticles have a well-separated core-shell structure or the core is rigid enough, the LCST of the nanoparticles should not be affected by the environmental pH since the pH-sensitive moieties were in the hydrophobic segments. The core-shell nanoparticles made from these polymers might be loosely packed. Thus, the core of the nanoparticles might be well accessible to the external environment. With the increase of pH of the external environment, the carboxylic acid groups in the 10-undecenoic acid segment was more de-protonated and thus reduced the hydrophobicity of the 10-undecenoic acid segment. This might lead to the increase in the LCST of polymers and thus lead to an increased LCST of the nanoparticles. In spite of having a similar content of carboxylic acid groups in Polymer I and Polymer II, the effect of de-protonation of carboxylic acid groups on the pH sensitivity of Polymer II was more significant than Polymer I. It may be because Polymer I had a higher molecular weight. The entropy of mixing decreases with an increased molecular weight as the thermodynamic phase separation across the LCST is caused by low entropy of mixing [Stile et al. Biomacromolecules 3 (2002) 591-600; Lessard et al., Can. J. Chem. 79 (2001) 1870-1874]. This indicates that the molecular weight is an important factor to influence the pH-sensitivity of polymers.

A further increase in the length of the hydrophilic segment led to greater LCST as shown in FIG. 6. Among the polymers, Polymer III with the NIPAAM/DMAAm/UA ratio of 3.5:1.75:0.5 provided core-shell nanoparticles of the highest LCST under all the pH conditions, which was higher than the normal body temperature. For instance, the LCST of Polymer III nanoparticles at pH 11.0, 7.4, 6.6, 6.0 and 5.5 was 43.0, 43.0, 41.0, 40.7 and 39.0° C., respectively. The LCST of Polymer III nanoparticles was also dependent upon pH. However, its temperature-sensitivity was low. This might be due to the dilution effect of DMAAm, that is, the PNIPAAm segments in the copolymer were well separated and diluted by DMAAm segments at the high molar ratio, which might reduce intramolecular hydrogen bonding between neighboring amide groups of NIPAAm. As a result, the temperature response of the copolymer was slow [Liu et al., J. App. Poly. Sci. 90 (2003) 3563-3568; Katsumoto et al., J. Phys. Chem. A. 106 (2002) 3429-3435].

Figure 7:
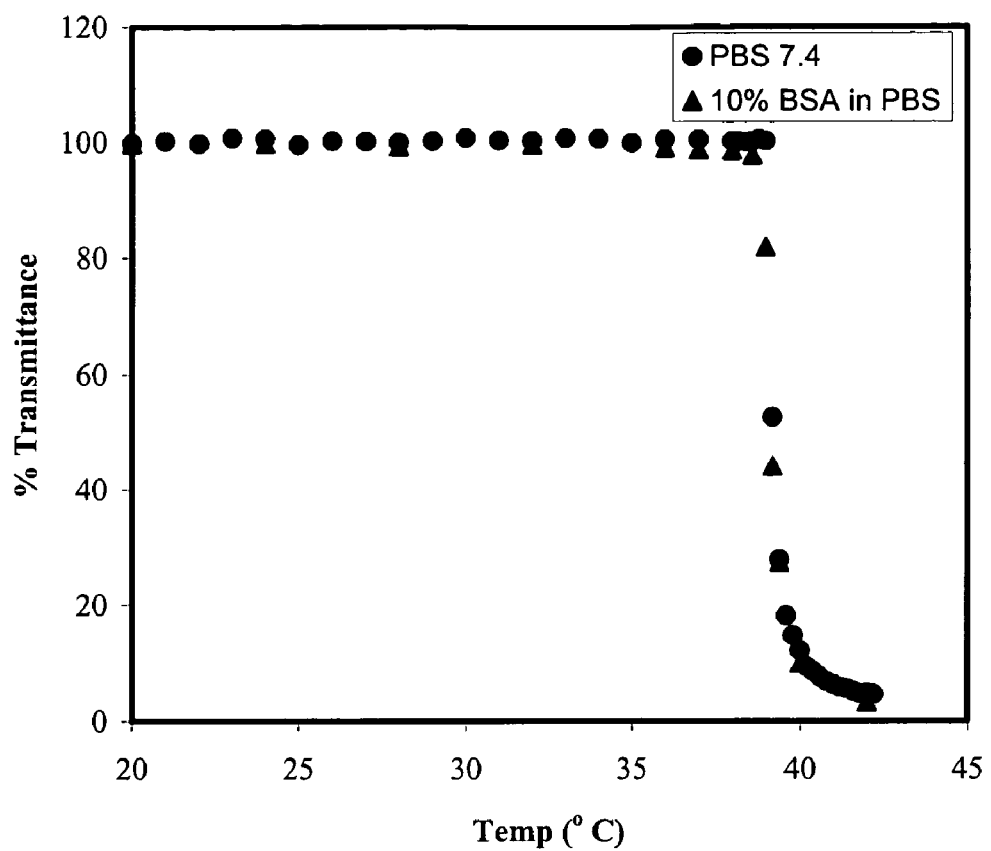
FIG. 7 depicts a plot of transmittance of Polymer II as a function of temperature in PBS (pH 7.4) with 10 (w/v) % BSA at 500 nm.

The effect of proteins on the LCST was investigated using Polymer II. As shown in FIG. 7, the presence of 10 wt % BSA did not alter the LCST of the core-shell nanoparticles.

These results show that the polymer can be designed with different LCST values above and bellow the normal body temperature in varying pH environments. The core-shell nanoparticles self-assembled from all the three polymers indeed showed pH-dependent LCST, which may be predominately triggered by the protonation or de-protonation of carboxylic acid groups in the hydrophobic segments of polymers. The LCST of the nanoparticles was very much influenced by the molar ratio of NIPAAm to DMAAm. In particular, the LCST of Polymer II nanoparticles was higher than the normal body temperature in the physiological environment (pH 7.4) but lower than the normal body temperature in slightly acidic environments. This means that the nanoparticles were soluble and stable in the physiological environment but destabilized/aggregated in acidic environments. This unique property may be utilized to target drugs to tumor tissues or cell interiors where the environment is characteristically acidic.

iii) CMC of Polymer II

Figure 8:
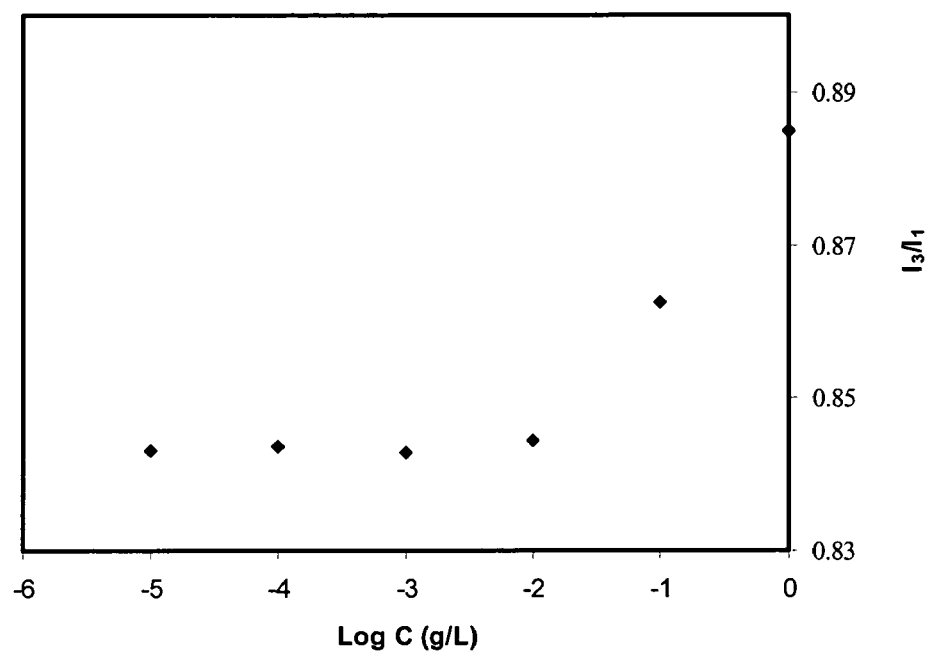
FIG. 8 depicts a plot of $I_3/I_1$ as a function of polymer concentration (Polymer II).
Figure 9:
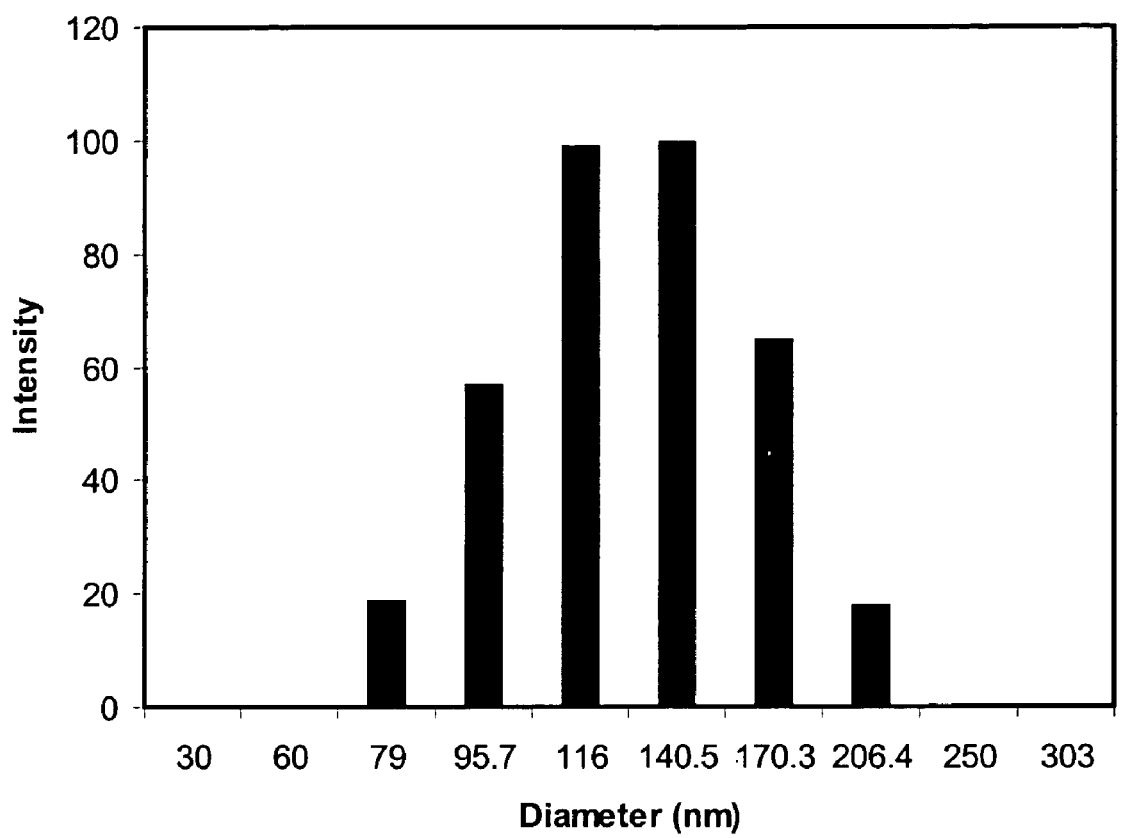
FIG. 9 depicts a typical presentation of the size distribution of DOX-loaded nanoparticles.
Figure 10:
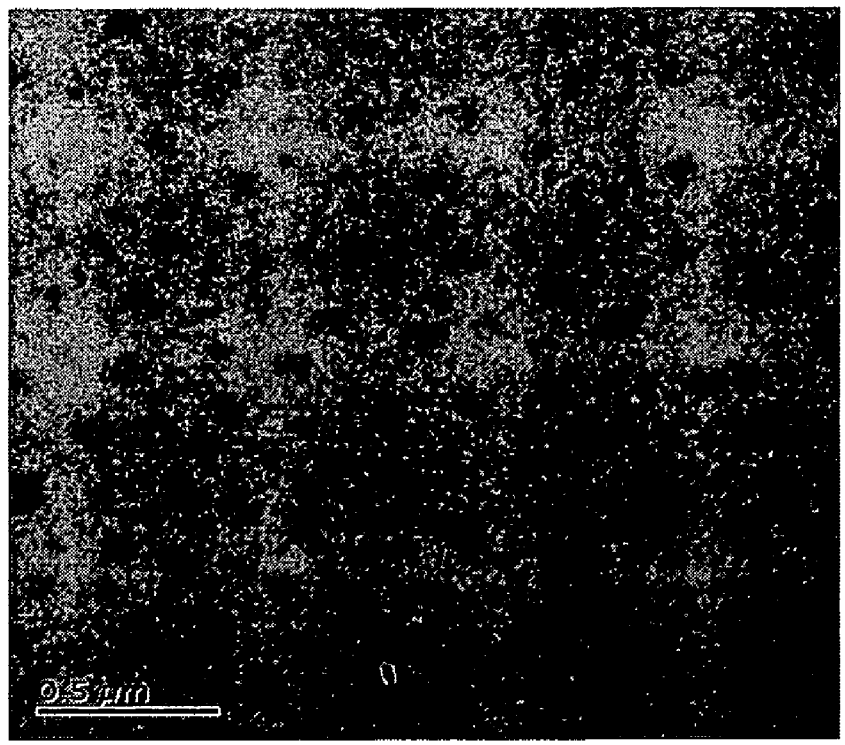
FIG. 10 depicts a TEM picture of drug-loaded nanoparticles.

The CMC is an important parameter to characterize the stability of core-shell nanoparticles. Above the CMC, amphiphilic polymer molecules can self-assemble into core-shell structured nanoparticles. The hydrophobic microenvironments of Polymer II nanoparticles in water were investigated by fluorescence spectroscopy using pyrene as a probe. The ratio of $I_3$ to $I_1$, was monitored as a function of polymer concentration. FIG. 8 shows plot of $I_3/I_1$ for Polymer II. A higher ratio is obtained when pyrene is located in a more hydrophobic environment [Dong et al. Can. J. Chem. 62 (1984) 2560-2565]. This property of pyrene can be utilized to study core-shell nanoparticle formation and deformation. The CMC value was determined to be approximately 10.0 mg/L. It is noticed that the change in $I_3/I_1$ after the formation of core-shell nanoparticles was small. This is probably because the core was loosely packed due to the presence of carboxylic groups and/or insufficient hydrophobicity of UA segments.

iv) Size Change of Polymer II Nanoparticles Induced by pH and Temperature Change The size of Polymer II nanoparticles was found to be pH-dependent. In 0.02 wt % HCl solution, the mean diameter of Polymer II nanoparticles was about 319 nm and in 0.02 wt % NaOH solution, the size of the nanoparticles decreased to about 240 nm. A significantly larger size of nanoparticles formed in the acidic solution indicates that nanoparticles in the acidic solution contained a higher degree of aggregation due to greater hydrophobicity of UA at low pH. On the other hand, the repulsion of de-protonated carboxylic acid groups at high pH led to a lower degree of aggregation, resulting in smaller size. The average size of the nanoparticles loaded with DOX was around 160-200 nm with a narrow size distribution as shown in FIG. 9. From the TEM picture (FIG. 10), the size of the nanoparticles was about 50-60 nm in the solid state, which might be due to the collapse of the free hydrophilic segments of the polymer as well as dehydration of the polymer chain. Meanwhile, it was observed that the nanoparticles were stable at pH 7.4 at 37° C. (below the LCST) and the size was around 265 nm. Heating the solution to 40° C. (above the LCST), the size increased to about 988 nm because of aggregation. The aggregates re-dispersed and the size reduced to the original level upon cooling. A similar phenomenon was observed for the nanoparticles at pH 6.6. These results further support the fact that the core-shell nanoparticles were both pH and temperature sensitive. The pH and temperature response was reversible.

The stability of the drug-loaded core-shell nanoparticles was investigated in PBS (pH 7.4) containing 10 (w/v) % BSA. There was a slight size increase (from 104 to 164 nm) after challenged with BSA for 7 hours. This initial size increase might be due to the hydration of freeze-dried nanoparticles. After hydration, the size returned back to the original level and kept unchanged for next three hours. This indicates that the nanoparticles were stable in the presence of BSA.

v) Cytotoxicity Study of Polymer II

Figure 11:
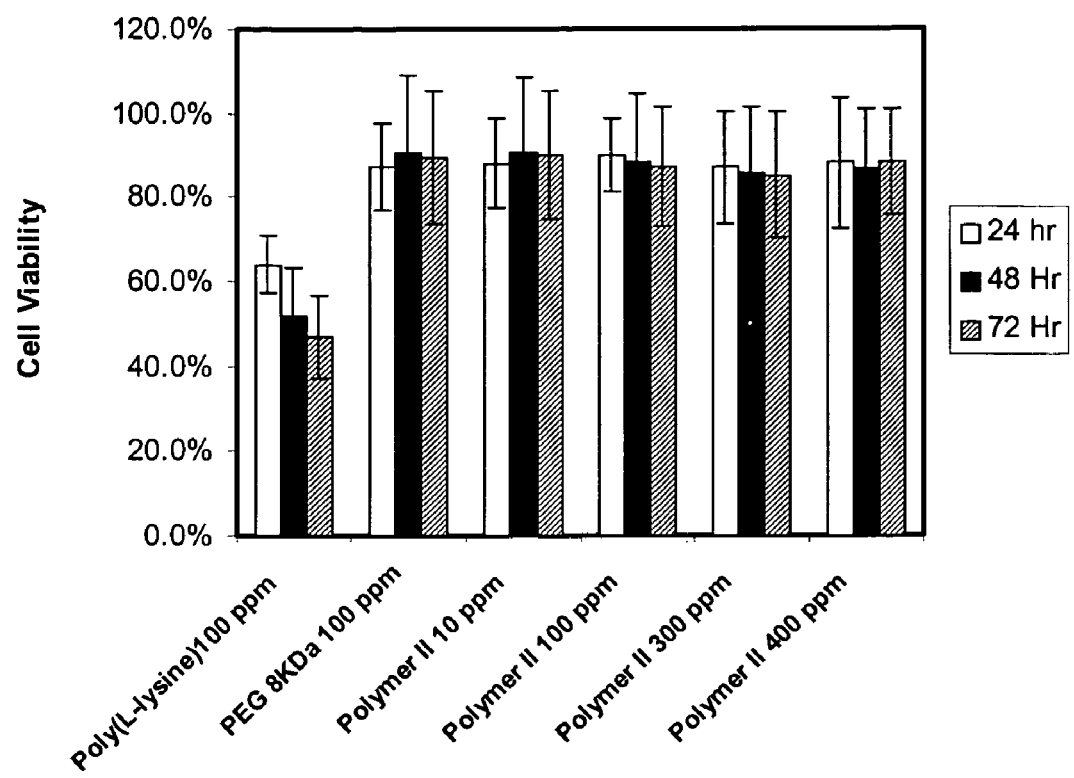
FIG. 11 shows the cytotoxicity of polymer II against L929 cells.

The L929 cells were exposed to the polymer at concentrations from 10 to 400 mg/L (ppm). From FIG. 11, there did not appear to be any significant cytotoxicity of the Polymer II samples as compared to the negative control. By 72 hours, all the samples of Polymer II appeared to be less cytotoxic than the positive control.

vi) In Vitro Release

Figure 12:
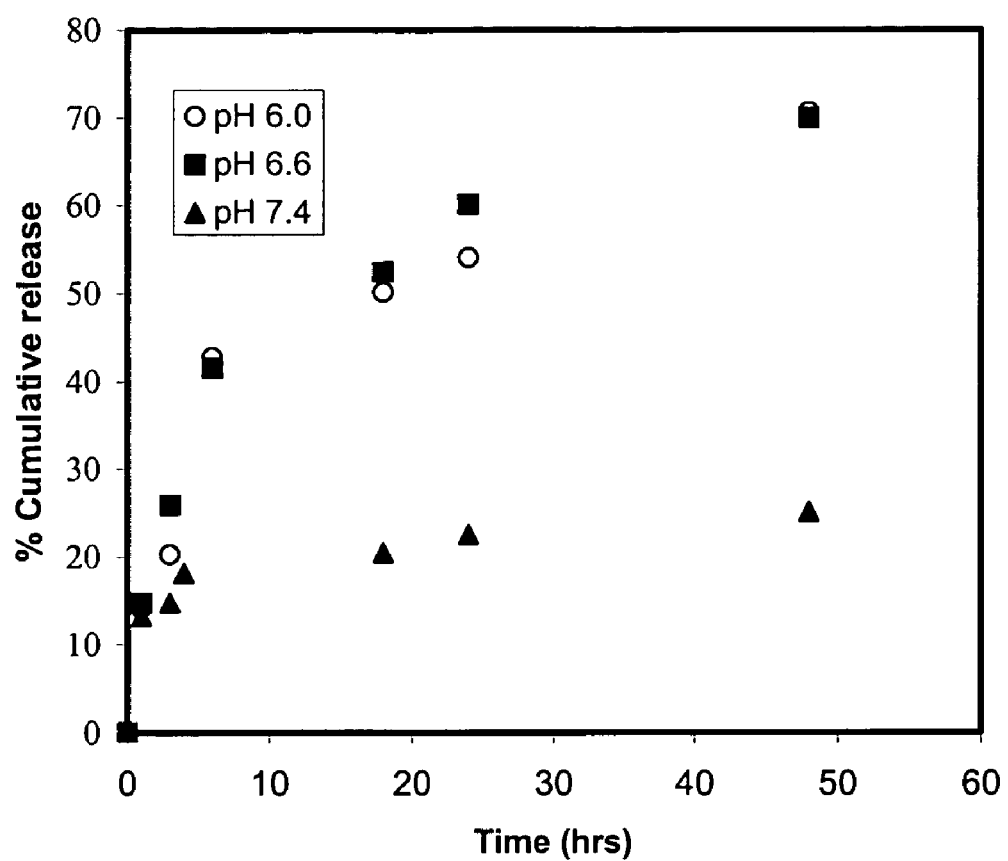
FIG. 12 shows the release profiles of DOX from Polymer II nanoparticles at varying pH at 37° C.

Under the fabrication conditions employed in this study, the actual loading level of DOX was about 2.7% in weight. In vitro drug release study was performed in a slightly acidic environment (pH 6.0 and 6.6) to simulate the pH of the tumor and in the physiological environment (PBS, pH 7.4). The release profiles of DOX are shown in FIG. 12. The drug release from the nanoparticles in pH 7.4 at 37° C. was considerably slow with an initial burst of about 18%. This initial burst might be due to drug molecules present in the shell of the nanoparticles. However, the drug release was much faster at pH 6.0 and 6.6 at 37° C. About 70% of the drug was released within 48 hours of study. In addition, it was observed that the drug-loaded nanoparticles were well dispersed in the buffer at pH 7.4 but aggregated and settled at the bottom of the dialysis bag at pH 6.0 and 6.6. These results show that the nanoparticles were indeed pH sensitive and slight change in pH from 7.4 to 6.6 or 6.0 led to the deformation and precipitation of the drug-loaded core-shell nanoparticles, thereby releasing the enclosed drug content. In addition, the release of DOX from the dialysis bag was studied at pH 7.4 and 6.0. There was no significant effect of pH observed, which further confirms that the pH-dependent release of DOX from the nanoparticles is mainly due to the pH responsiveness of the nanoparticles rather than drug solubility.

C) Conclusions

Amphiphilic tercopolymers poly(N-isopropylacrylamide-co-N,N-dimethylacrylamide-co-10-undecenoic acid) with various compositions was synthesized by free-radical solution polymerization with free amine end group. The core-shell nanoparticles self-assembled from the polymer with the NIPAAm/DMAAm/UA ratio of 3.75:1.25:0.5 were of LCST well above the normal body temperature at pH 7.4 and much lower than the normal body temperature in slightly acidic environments. The polymer did not show significant cytotoxicity for a period of up to 72 hours. The DOX-loaded nanoparticles were stable at pH 7.4 at 37° C. and the size was about 160-200 nm. However, at pH 6.0 and 6.6, the structure of the nanoparticles was deformed, thereby releasing the enclosed drug molecules. These properties might help in selective accumulation of the nanoparticles and selective release of the drug in acidic tumor tissues. One more advantage of the polymer synthesized is that the polymer is with a free amine functional group, which might allow further modification of the polymer by attaching biological signals for active targeting.

EXAMPLE 2

Figure 13:
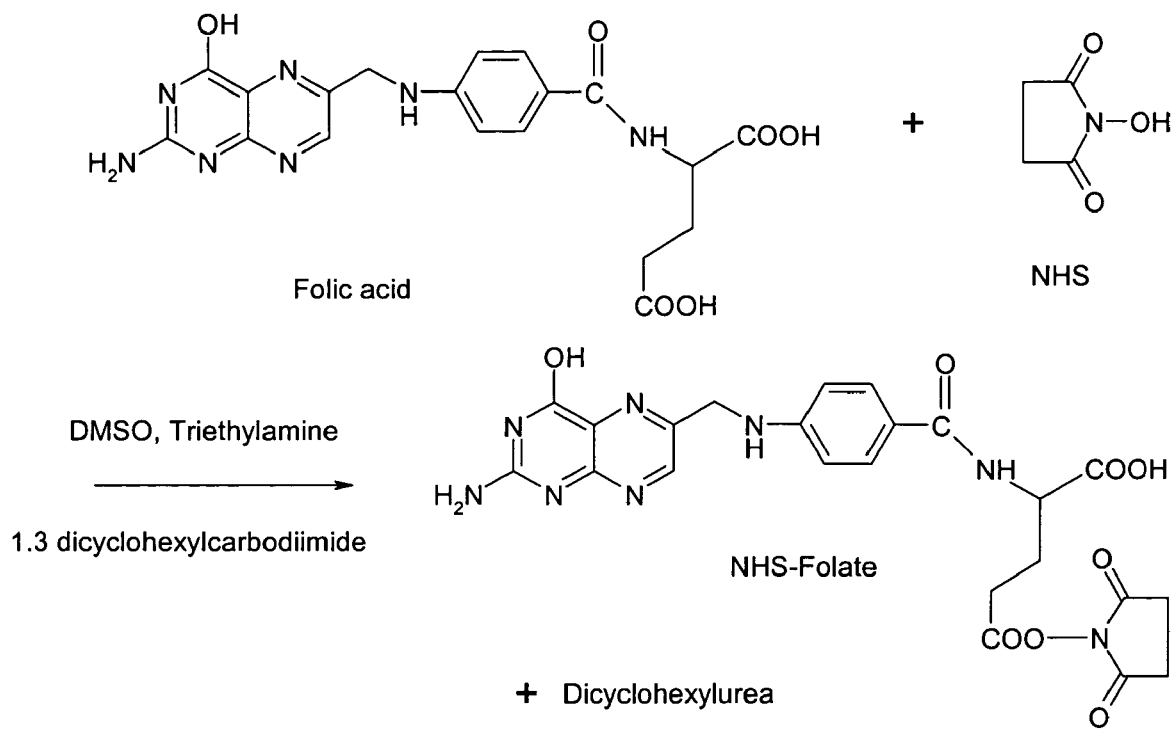
FIG. 13 shows Scheme 2, which illustrates the activation of folic acid with N-hydrosuccinimide (NHS).
Figure 14:
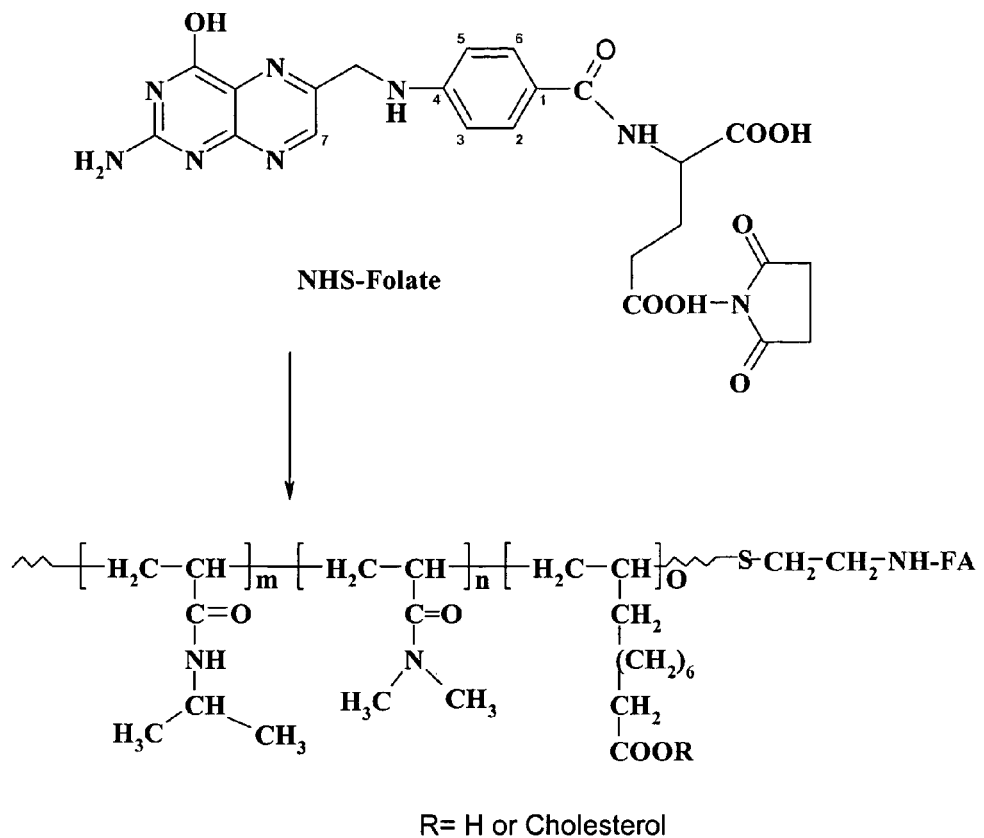
FIG. 14 shows Scheme 3, which illustrates the conjugation of folic acid to Polymer II.
Figure 15:
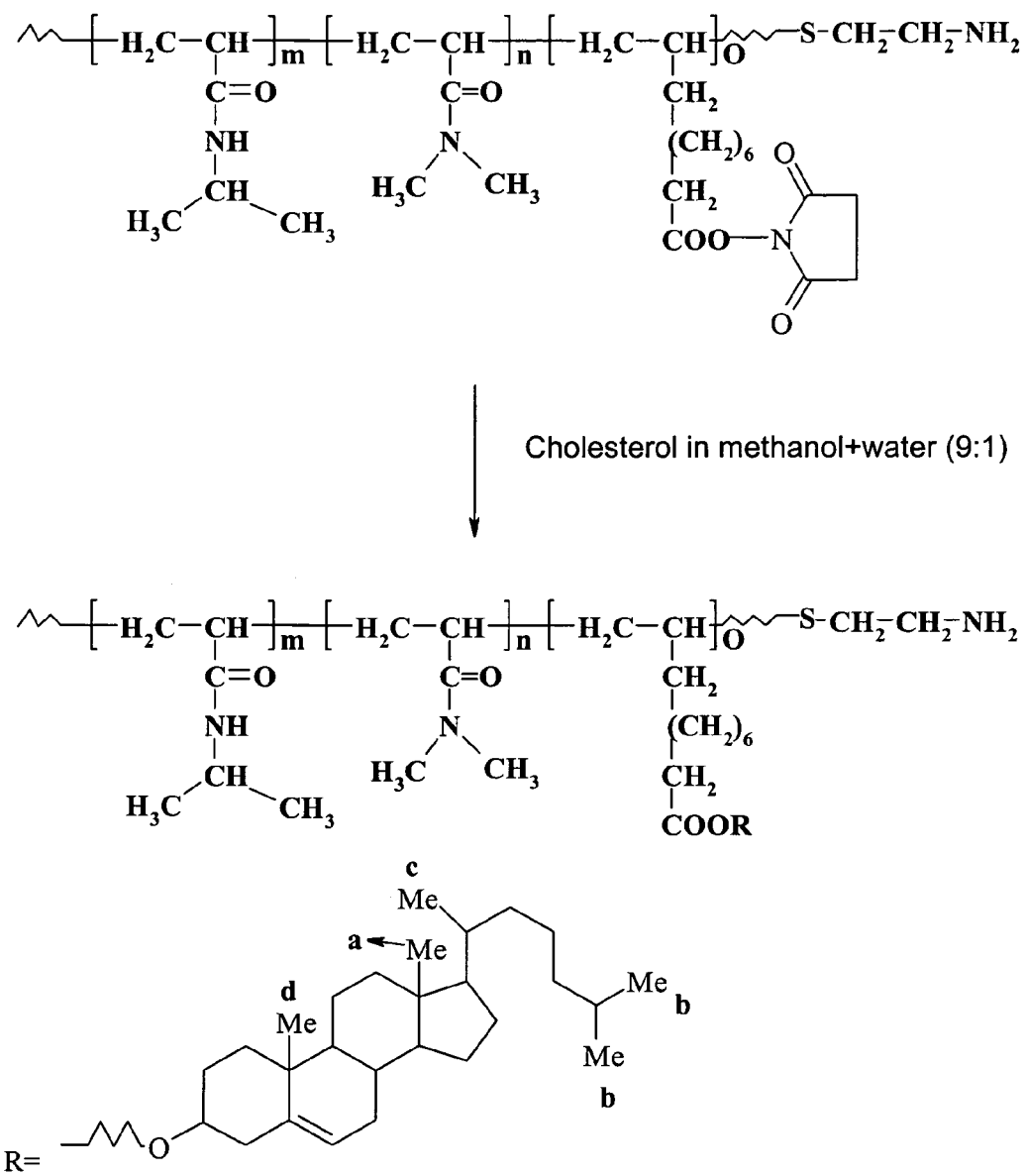
FIG. 15 shows Scheme 4, which illustrates the conjugation of cholesterol to polymer II via NHS activation.

Synthesis of poly(N-isopropylacrylamide-co-N,N-dimethylacrylamide-co-10-undecenoic acid) [P(NIPAAm-co-DMAAm-co-UA)]Having a Folate Targeting Group A) Experimental Section i) Materials Poly(N-isopropylacrylamide-co-N,N-dimethylacrylamide-co-10-undecenoic acid) [P(NIPAAm-co-DMAAm-co-UA), Polymer II] was synthesized by free radical polymerization as explained in Example 1. Folic acid dihydrate, N-hydroxysuccinimide (NHS), dicyclohexylcarbodiimide (DCC), dimethyl sulfoxide (DMSO) were purchased from Sigma, Aldrich. Paclitaxel was purchased from Merck.

ii) Conjugation of Folic Acid to P(NIPAAm-co-DMAAm-co-UA) and Conjugation of Folic Acid to P(NIPAAm-co-DMAAm-co-UA) Grafted with Cholesterol NHS ester of folic acid (NHS-folate) was prepared by the following method: folic acid (5 gm dissolved in 100 mL of DMSO plus 2.5 mL of triethylamine) was reacted with N-hydroxysuccinimide (2.6 g) in the presence of DCC (4.7 g) overnight at room temperature. The by-product, dicyclohexylurea was removed by filtration (as shown in FIG. 13, Scheme 2). To conjugate the folic acid to Polymer II (Poly-FA), the activated NHS-folate in DMSO was added to Polymer II in PBS buffer (pH 7.4) with constantly stirring for 5 hrs at room temperature (FIG. 14, Scheme 3). The folic acid-conjugated polymer was purified by dialysis in the presence of PBS buffer (pH 7.4) for 24 hrs and followed by ultra pure water for 24 hrs using dialysis membrane of molecular weight cut-off of 2000 (Spectra/Por). The polymer was freeze-dried and stored in an airtight container for further use. Folic acid was also conjugated to Polymer II grafted with cholesterol (Poly-CH-FA). Polymer II grafted with cholesterol (Poly-CH) was synthesized by reacting Polymer II activated with NHS (The procedure was similar to the activation of folic acid by using 1:2:2 molar ratio of polymer II, NHS and DCC respectively) with an equal molar concentration of cholesterol in the hydroalcoholic solution for 48 hrs at room temperature (FIG. 15, Scheme 4).

Chemical structure of the polymers was characterized by $^1$H NMR (Bruker AVANCE 400) and Fourier transform infrared (Perkin Elmer Spectrum 2000, KBr) spectroscopic methods. Differential scanning calorimetry (DSC) experiments were performed using a TA 2920 Modulated DSC instrument (CT, USA) with a ramp speed of 3° C./min.

iii) Preparation of Drug-Loaded Polymer-CH-FA Core-Shell Nanoparticles

Doxorubicin was loaded in the core-shell nanoparticles as follows: 7.5 mg or 5.0 mg of DOX was dissolved in 3 mL of DMAc or DMF with stirring. 15 mg of polymer was then dissolved in the solution. The mixture was dialyzed against 500 mL of de-ionized water for 48 hours. To determine DOX loading level, a known amount of DOX-loaded nanoparticles was dissolved in 1 mL of methanol and then diluted with PBS. The DOX concentration was estimated by using the UV-VIS. Initial study was also performed by loading the core-shell nanoparticles with paclitaxel, a water insoluble anti-cancer drug. Briefly, 15 mg of the polymer and 2.5 mg of paclitaxol was dissolved in 3 mL of DMF, the polymer drug solution was dialyzed in the presence of ultra pure water for 24 hrs. The drug-loaded nanoparticles were filtered through a disc filter of 0.45 μm pore size and freeze-dried. To determine loading level of paclitaxol, paclitaxol was extracted from the polymeric nanoparticles by dissolving the nanoparticles in 1 mL of chloroform, and the polymer was precipitated by adding 2 mL of diethyl ether. After centrifuge, the supernatant was collected, dried and analyzed by HPLC (Waters, model 2690, C8 15×4.6 cm column). The mobile phase consisted of 20 mM ammonium acetate, acetonitrile and methanol in the volume ratio of 35:45:20. The standard paclitaxol solutions were prepared in methanol with concentrations ranging from 5 to 100 ppm.

B) Results and Discussion

Figure 16:
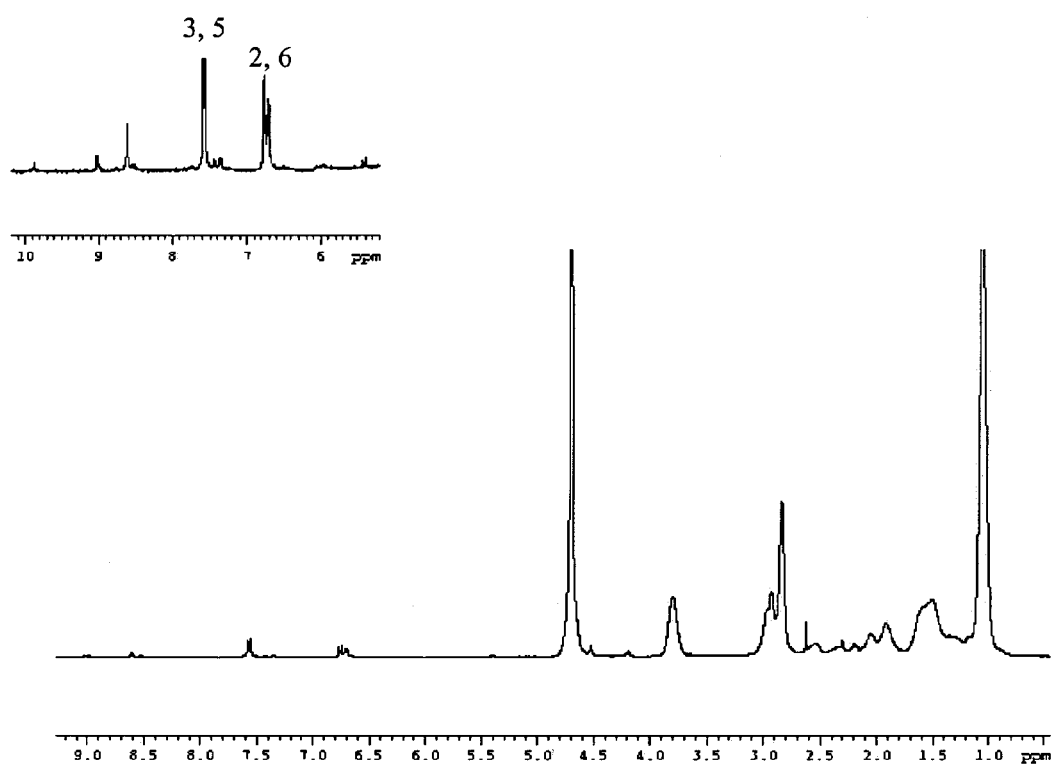
FIG. 16 shows the NMR spectrum of folic acid-conjugated Polymer II.
Figure 17:
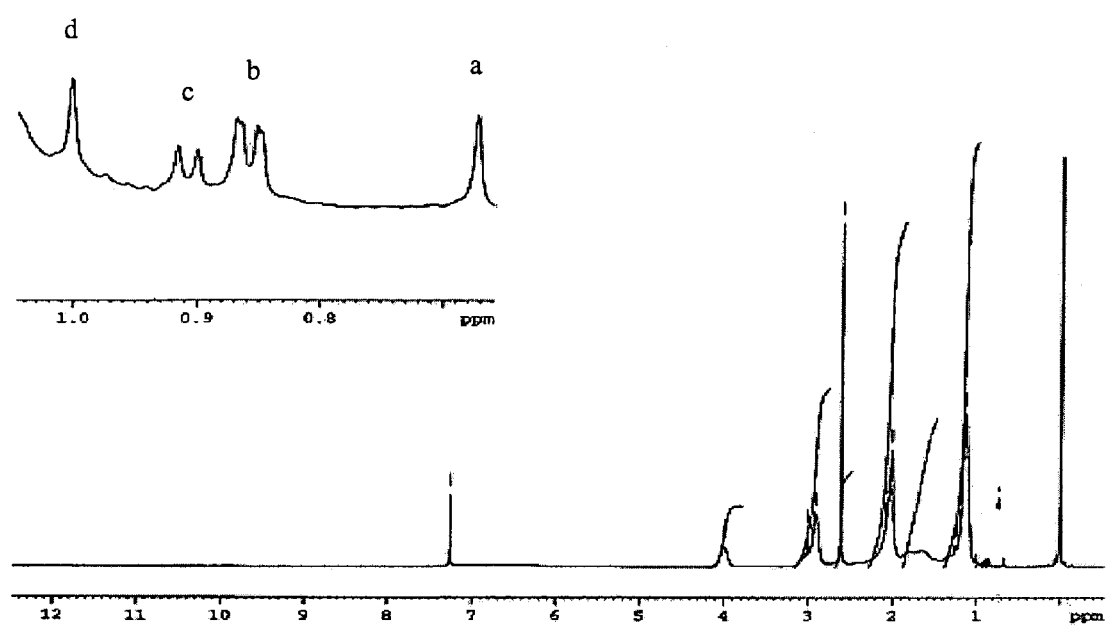
FIG. 17 shows the NMR spectrum of cholesterol-grafter Polymer II.

Folic acid was conjugated successfully to Polymer II and polymer II grafted with cholesterol. This is confirmed by NMR studies (FIGS. 16 and 17). The success of the conjugation of folic acid was evidenced by the presence of proton signals at δ 6.6-6.8 and δ 7.5-7.7 from the aromatic protons 2, 6 and 3, 5 in the folic acid molecule (FIG. 14, Scheme 3). The conjugation of the cholesterol on to Polymer II was also evidenced by the proton signals (δ 0.6-1.1) from the five $CH_3$ groups of cholesterol.

Figure 18:
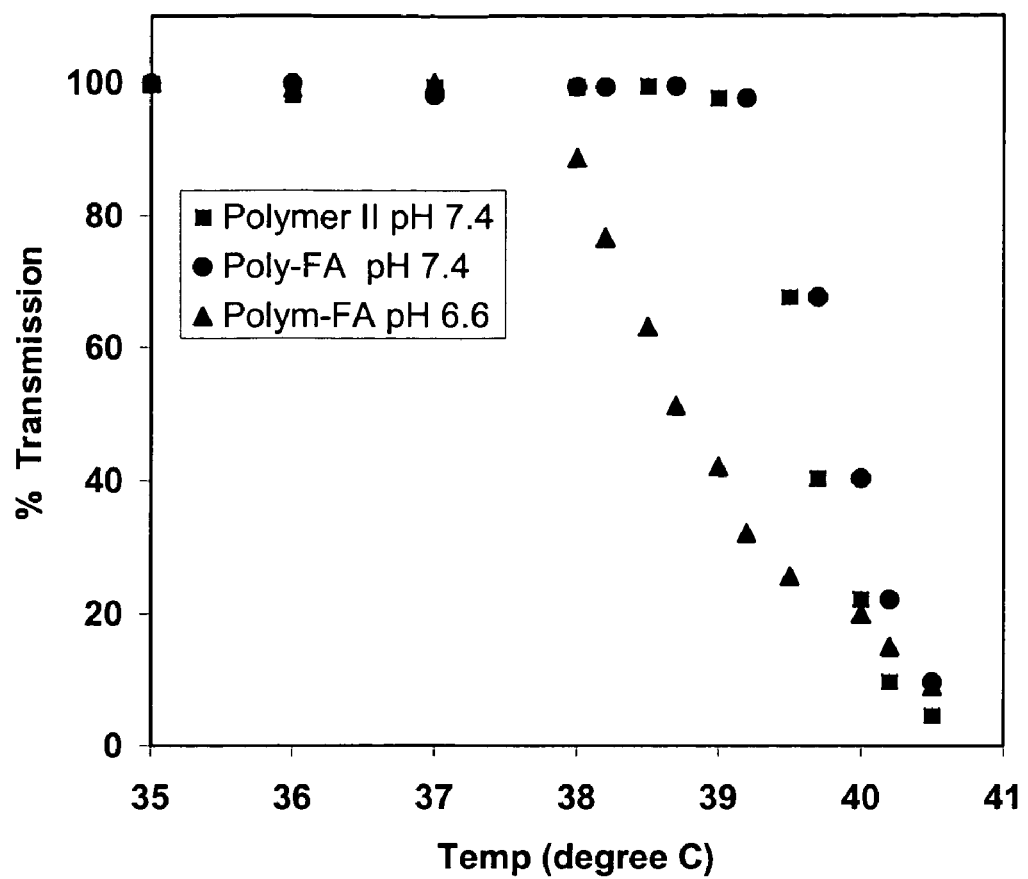
FIG. 18 shows the optical transmittance of poly-folic acid and Polymer II as a function of temperature at various pH at 500 nm.
Figure 19:
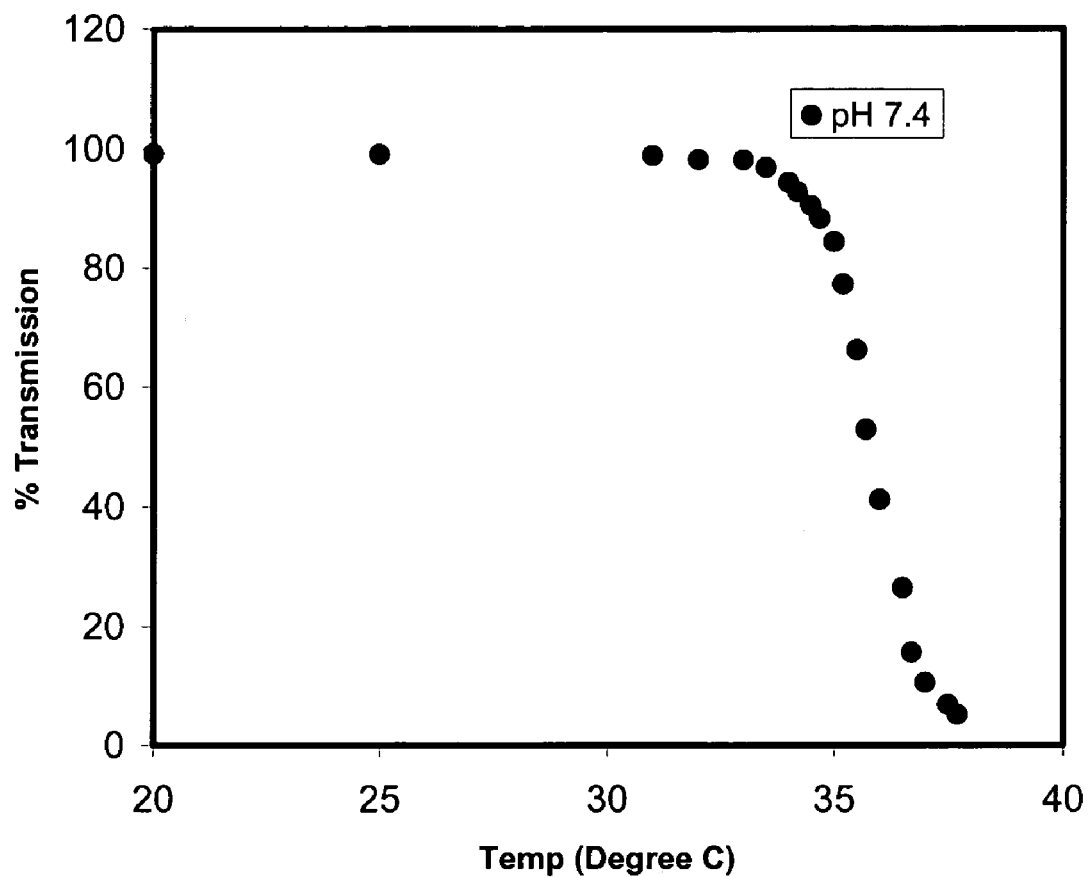
FIG. 19 shows the optical transmittance of poly-cholesterol as a function of temperature at a pH of 7.4 at 500 nm.
Figure 20:
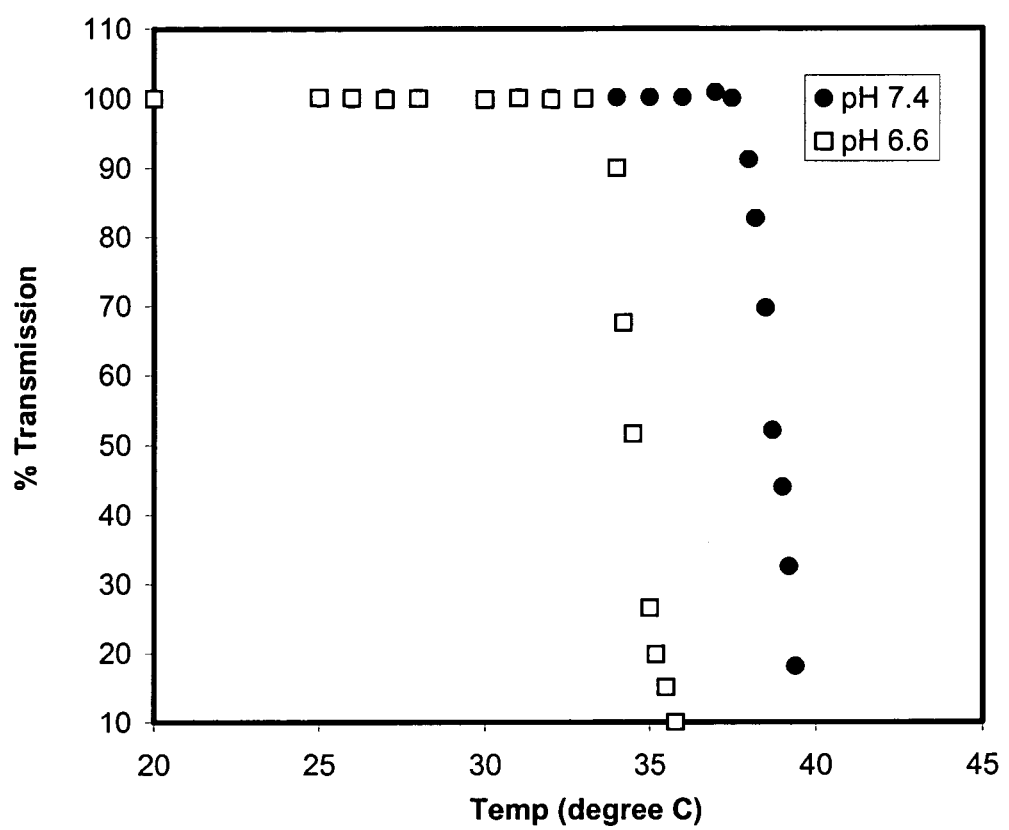
FIG. 20 shows the optical transmittance of poly-cholesterol-folic acid as a function of temperature at different pH at 500 nm.

From Example 1, the LCST of Polymer II was 38.5° C. at pH 7.4, which decreased to 35.5° C. at pH 6.6. This is due to the protonation and deprotonation of the polymer with the change in pH, which changes the hydrophobicity of the polymer. There was no significant difference in the LCST at pH 7.4 between Poly-FA and Polymer II. However, there was an increase in the LCST at pH 6.6, and the temperature sensitivity was lower (FIG. 18). This might be due to the fact that folic acid increased the hydrophilicity of the polymer at this pH. However, the solubility of the polymer in pH 5.0 was low and the solution was turbid. The LCST of the polymer decreased to 36° C. and the temperature sensitivity was higher (data not shown). This might be due to the fact that folic acid has a pKa around pH 5.4, its carboxylic functional groups were protonated at pH 5.0, increasing the hydrophobicity of the polymer. This property may help in intracellular delivery of drugs due to the LCST lower than normal body temperature at pH 5.0 (in endosomes), which may help break down the endosome membrane. When cholesterol was conjugated to Polymer II, the LCST of the polymer was 35.7° C. at pH 7.4 as shown in FIG. 19, which was lower than Polymer II. This is because grafting cholesterol increased the hydrophobicity of the polymer, decreasing the LCST. On the other hand, the LCST of Poly-CH-FA was 39.0 and 34.5° C. at pH 7.4 and pH 6.6 respectively (FIG. 20). This might be due to the fact that the increase in the hydrophobicity of the polymer caused by the introduction of cholesterol was equally compensated by the folic acid molecule.

Figure 21:
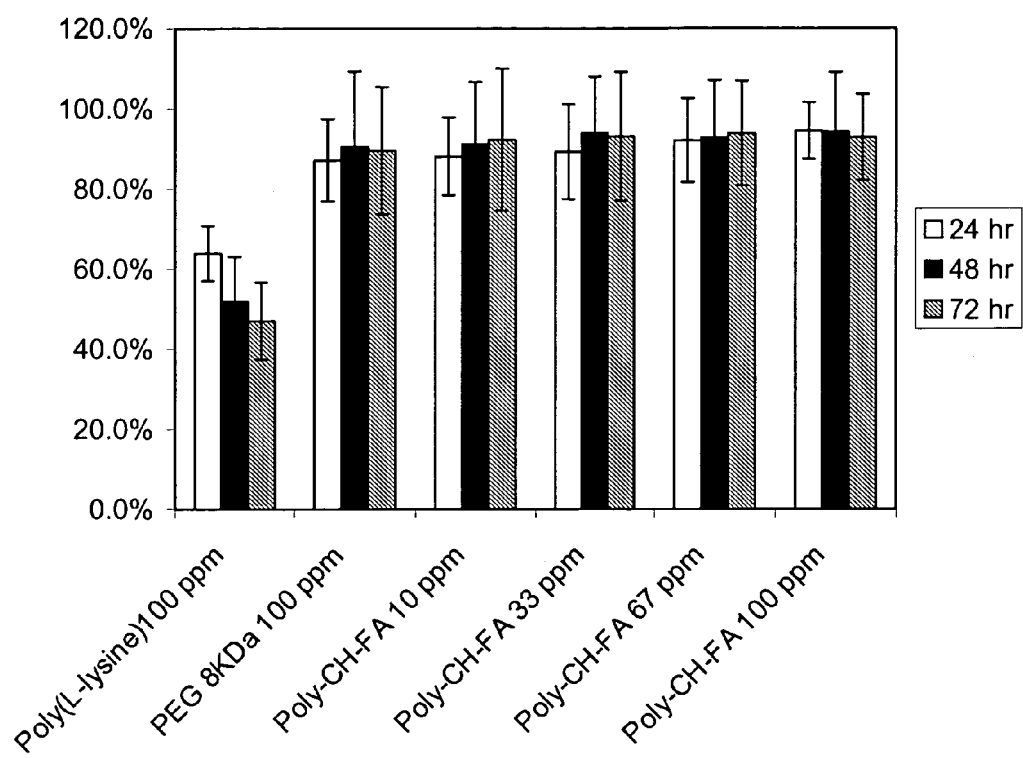
FIG. 21 shows bar charts depicting the cytotoxicity of poly-cholesterol-folic acid against L929 cells.

ATCC L929 cells were exposed to the polymer at concentrations from 10 to 100 mg/L (ppm). From FIG. 21, there did not appear to be any significant cytotoxicity of the Poly-CH-FA samples as compared to the negative control [poly(ethylene glycol)]. However, all the samples of Poly-CH-FA were less cytotoxic than the positive control [poly (L-lysine)].

A typical dialysis method was used to prepare Poly-CH-FA empty and drug-loaded core-shell nanoparticles. Doxorubicine hydrochloride and paclitaxol were selected as water-soluble and water-insoluble drugs. The effect of the solvent on the drug loading of doxorubicine was studied. With the use of DMAc, there was an encapsulation efficiency of 12.9% with drug loading of 4.31% in weight. The average diameter of particles was about 265 nm. However, in the case of the dialysis method where DMF was used as the solvent, the drug loading was decreased to 0.6% with an encapsulation efficiency of 2.4% and an average particle size of 100 to 160 nm. The decreased drug loading in the later formulation might be due to the fact that the solubility of the DMF was higher (12.1 cal/cm$^3$) compared to DMAc (10.8 cal/cm$^3$), which might help in the early escape of the drug before getting encapsulated. The decreased particle size might be attributed to decreased drug loading.

Figure 22:
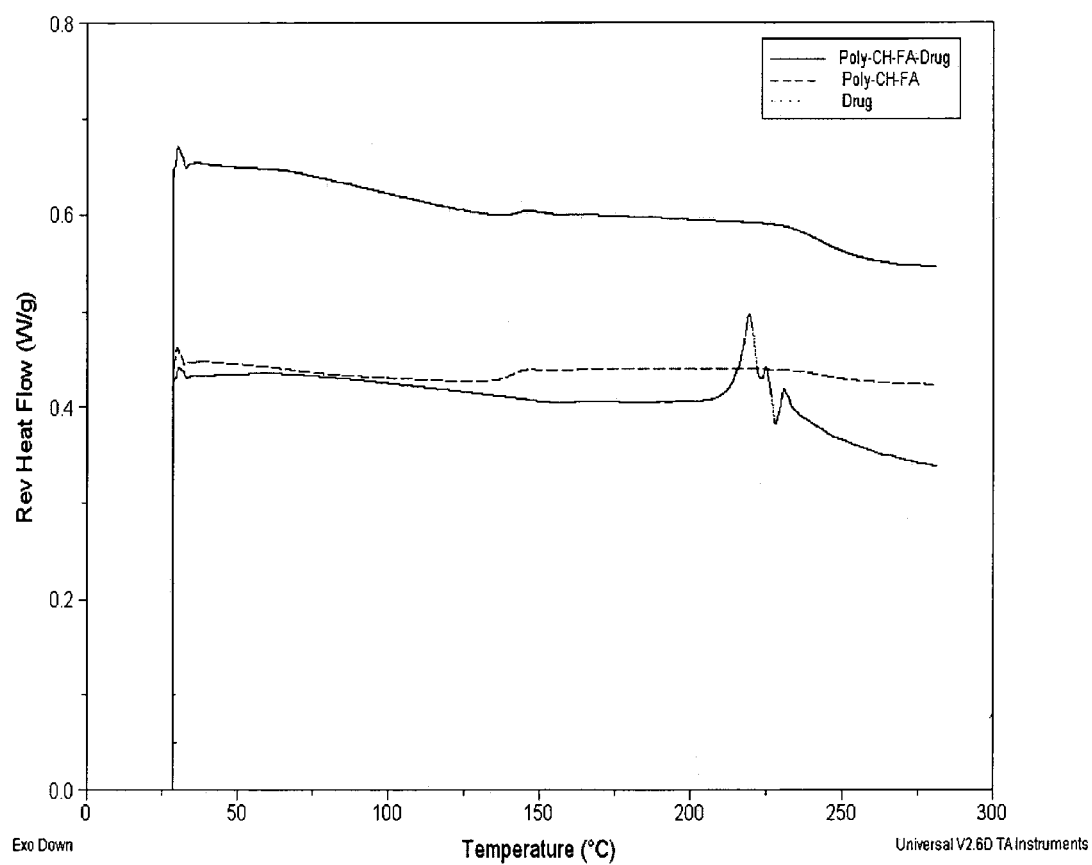
FIG. 22 shows the DSC analyses of the copolymer, paclitaxol and paclitaxol-loaded core-shell nanoparticles.

Paclitaxol was loaded into the core-shell nanoparticles with an average particle size of 96 nm, an encapsulation efficiency of 13.0% and a drug loading of 1.9%. Paclitaxol is a crystal drug with a melting point of 220° C. (FIG. 22). The melting point of paclitaxol disappeared after encapsulated in the nanoparticles, indicating that the drug was molecularly distributed.

C) Conclusion

Core-shell nanoparticles with an active targeting signal (folic acid) to tumor cells was synthesised. The nanoparticles retained the pH sensitive property, and possessed low cytotoxicity. Two anticancer drugs were loaded into the core-shell nanoparticles. The particle size and loading level of drugs can be manipulated by varying fabrication conditions.

EXAMPLE 3

Synthesis of Doxorubicin Conjugated poly(N-isopropylacrylamide-co-N,N-dimethylacrylamide-co-10-undecenoic acid) [P(NIPAAm-co-DMAAm-co-UA)]

i) Conjugation of Doxorubicin to Copolymer

Figure 25:
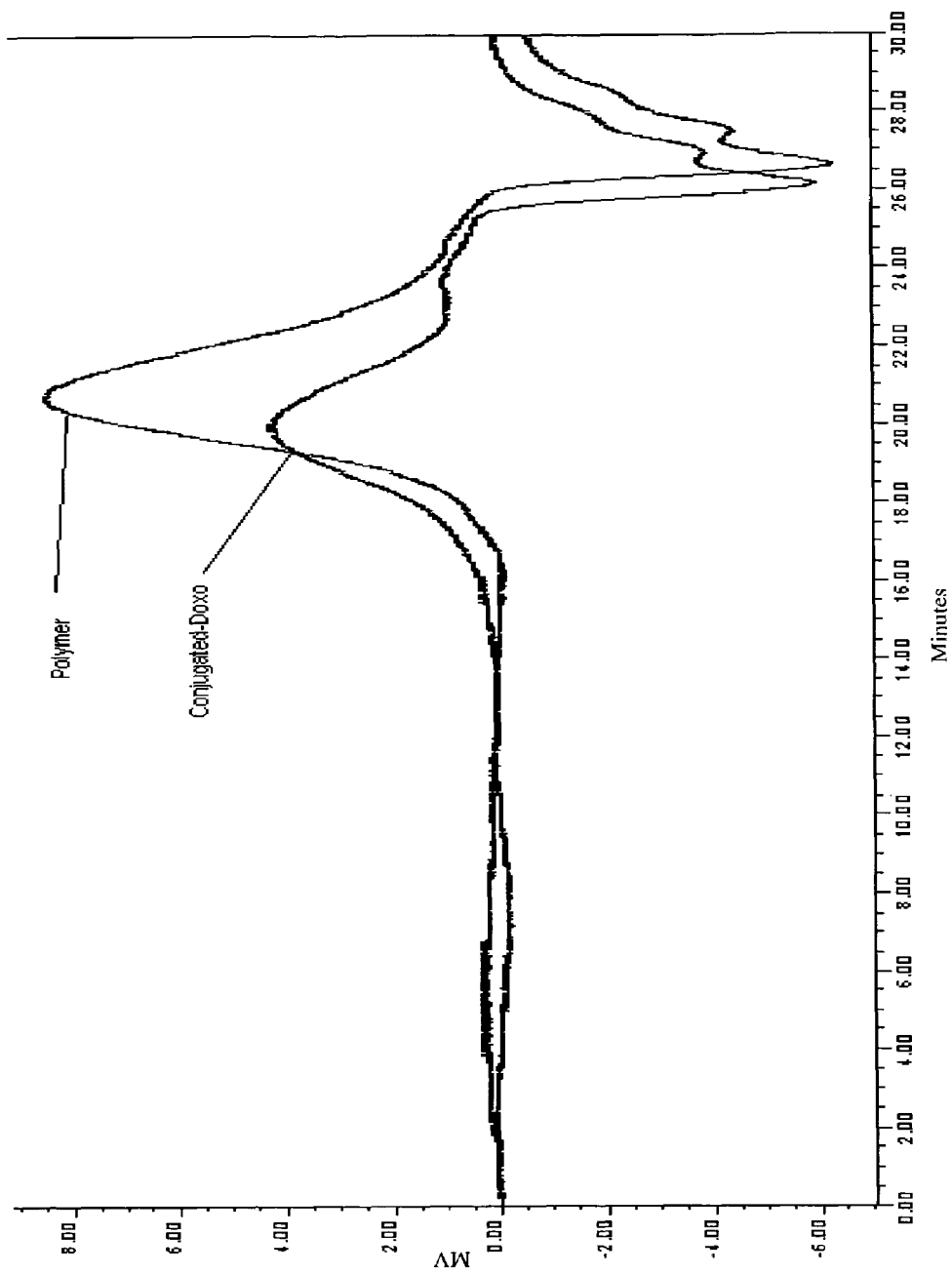
FIG. 25 shows the gel permeation chromatogram of doxorubicin conjugated Polymer II.
Figure 26:
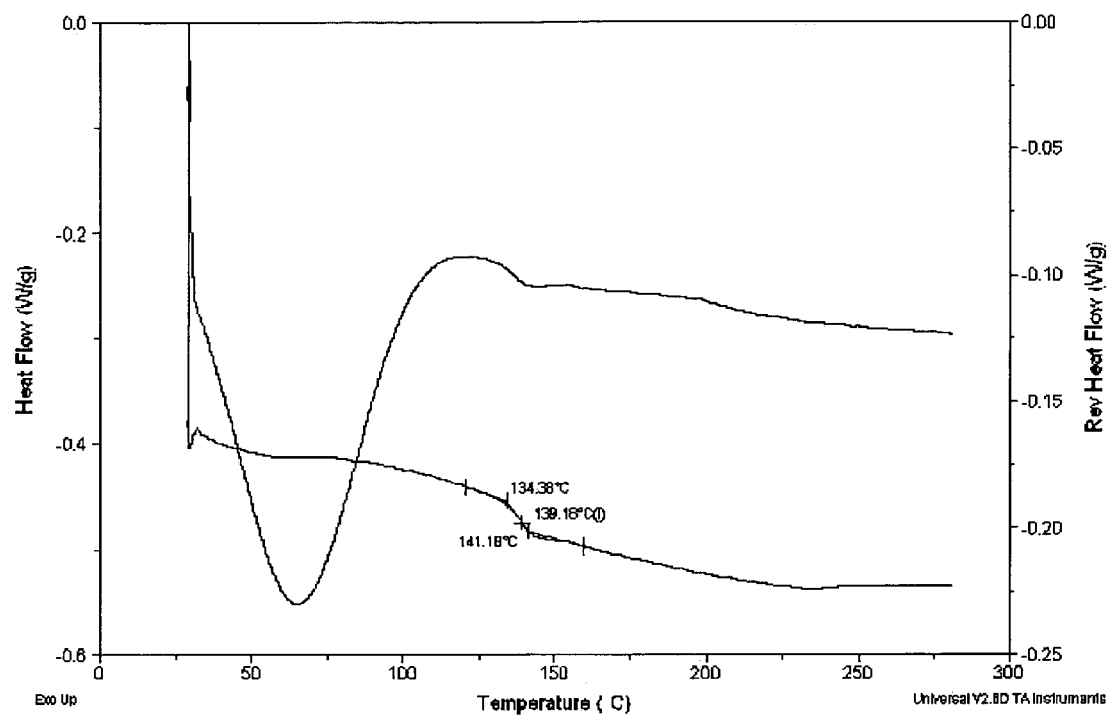
FIG. 26 shows the differential scanning calorigram of doxorubicin conjugated Polymer II.

Polymer II can also be conjugated to drugs which are having reactive functional groups. Doxorubicin (FIG. 23) was conjugated through carbodiimide chemistry wherein the amine functional group of doxorubicin was conjugated to carboxyl functional groups of polymer II, as presented in FIG. 24. Briefly, polymer II conjugated with doxorubicin (Poly-DOX) was synthesized by reacting the polymer II activated with NHS (procedure was similar to activation of folic acid described in Example 2) with doxorubicin (its concentration was two times as high as that of polymer II.) in phosphate buffer (pH 7.4) for 48 hrs at room temperature. The blood red colored product was obtained after dialyzing in the presence of ultra pure water for 48 hours using a dialysis membrane with a 2000 molecular weight cut-off, followed by freeze-drying. It is confirmed from the gel permeation chromatography that there was an increase in the molecular weight of the polymer II from Mw: 9,051, Mn: 6,781 to Mw: 11,129, Mn: 9,118, and also a decrease in the retention time as shown in FIG. 25. Moreover, the differential scanning calorimetry of the conjugate shows that there was no appearance of transition for melting point of doxorubicin at 202° C. (as shown in FIG. 26), which indicates that drug was part of the polymer chain.

ii) Fabrication of Micelles from the Doxorubicin Conjugated Polymer II

Figure 27:
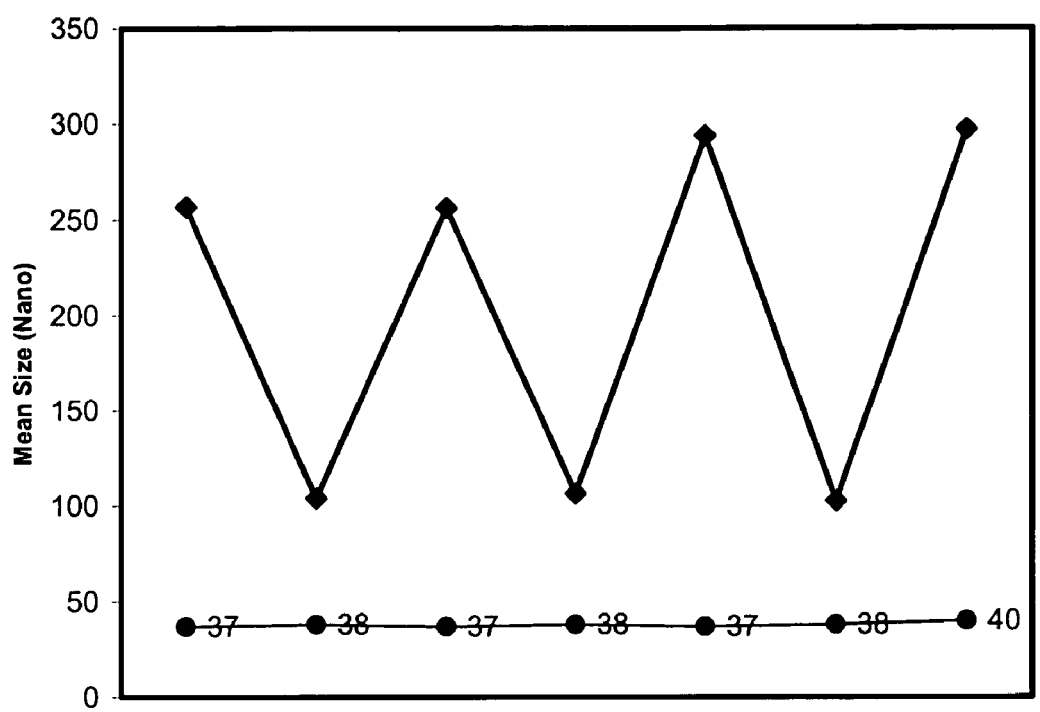
FIG. 27 shows the temperature sensitive reversible particle size of a drug conjugated micelle in PBS at a pH of 7.4.

After conjugation of the drug on to the polymer chain, it was observed that the polymer was relatively insoluble in water. It was attempted to prepare core-shell nanoparticles (micelles) using this polymer by both dialysis as well as solvent evaporation methods. It was found that dialysis was not a suitable method as the polymer is more hydrophobic, leading to the precipitation of the polymer or formation of bigger particles in the range of 800-1000 nm. However, by using the solvent evaporation method, it was able to produce micelles with a mean diameter of 280 nm. Procedure for solvent evaporation was as follows: 15 mg of the conjugated polymer was dissolved in 4 mL of dimethylacetamide and 1 mL of dichloromethane, and the polymer solution was emulsified into 20 mL of ultra pure water and sonicated for 5 mins. The solvent was evaporated and the solution was centrifuged and measured for particle size. Conjugation of the drug to the micelle did alter the pH triggered temperature sensitivity of the polymer. It was observed that there was a decrease in the particle size above 38° C. (above the LCST), which might be due to the collapse of the temperature sensitive segment in pH 7.4. This phenomenon was found to be reversible and reproducible (FIG. 27).

EXAMPLE 4

Synthesis of Block Copolymer poly(N-isopropylacrylamide-co-N,N-dimethylacrylamide)-b-poly(10-undecenoic acid) [P(NIPAAm-co-DMAAm)-b-PUA]

Figure 28:
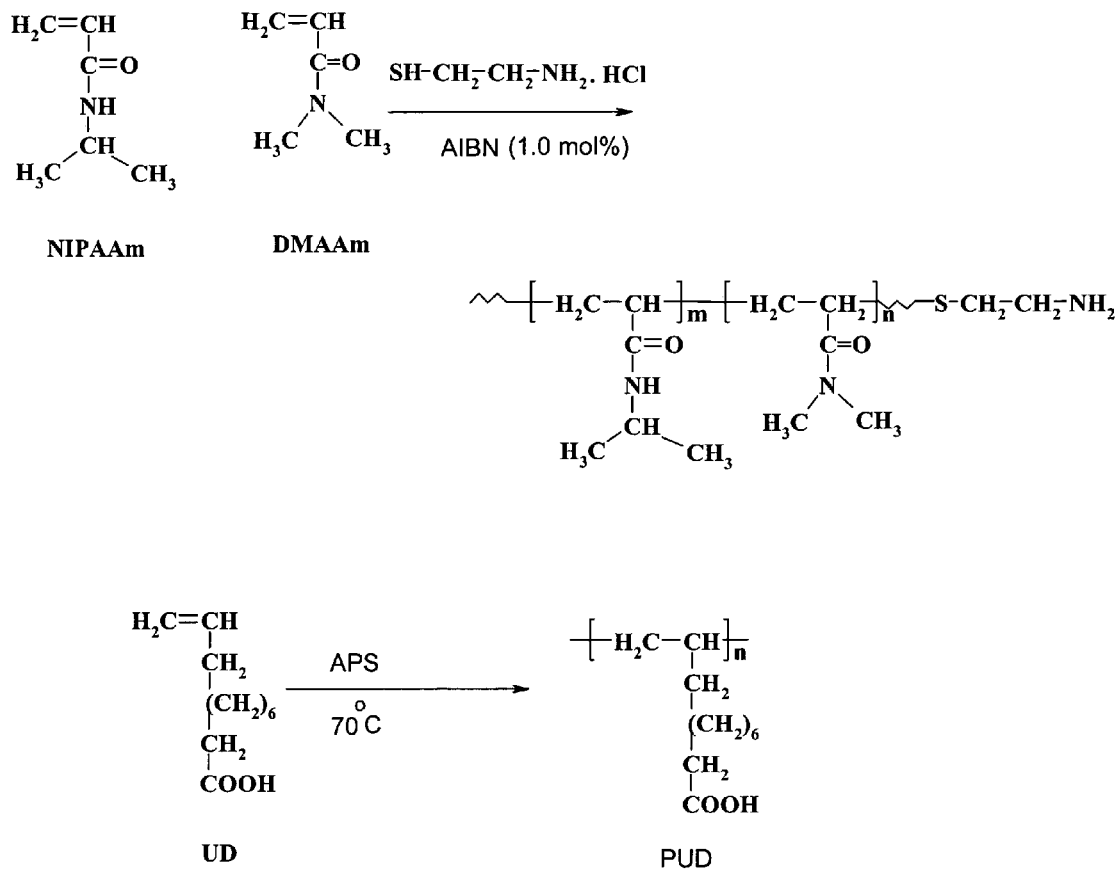
FIG. 28 shows Scheme 5, which illustrates the synthesis of the temperature block consisting of NIPAAm and DMAAm, and the synthesis of poly (10-undecenoic acid).
Figure 29:
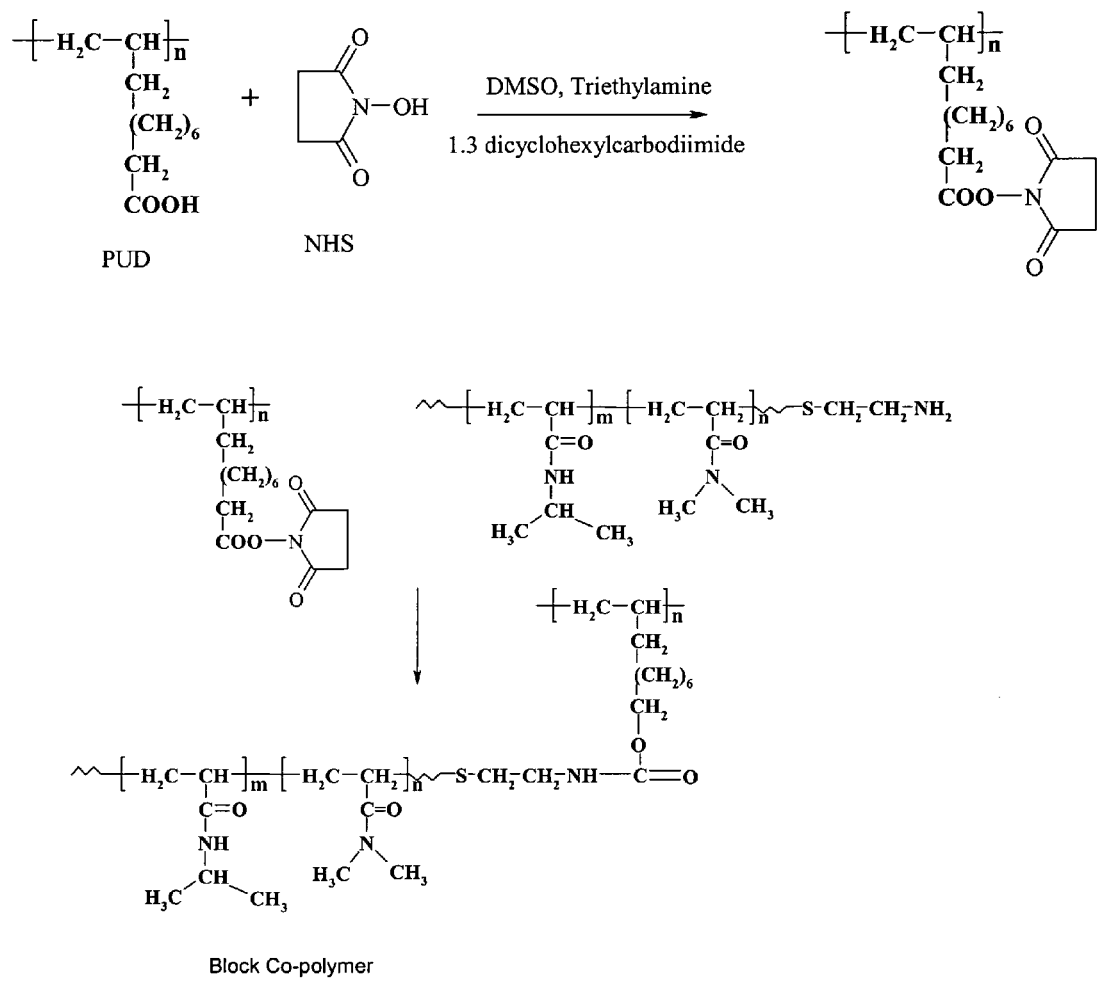
FIG. 29 shows Scheme 6, which illustrates the synthesis of a block copolymer.
Figure 30:
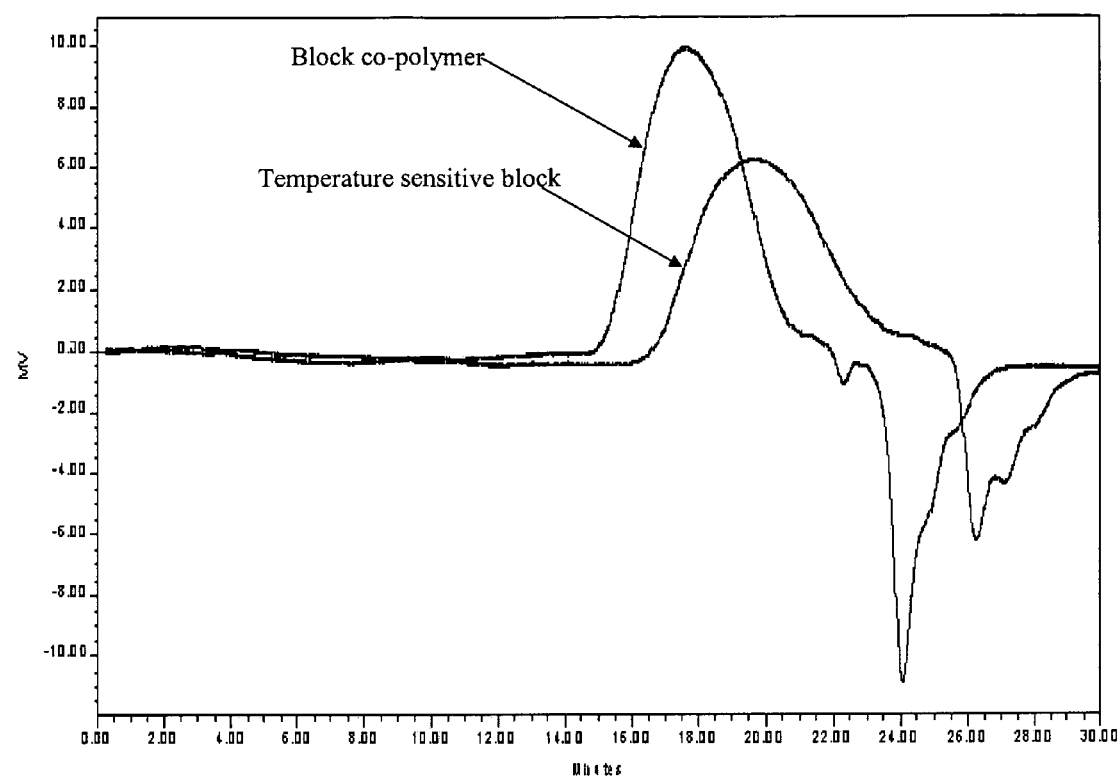
FIG. 30 shows the gel permeation chromatogram of temperature sensitive block and of the block copolymer.
Figure 31:
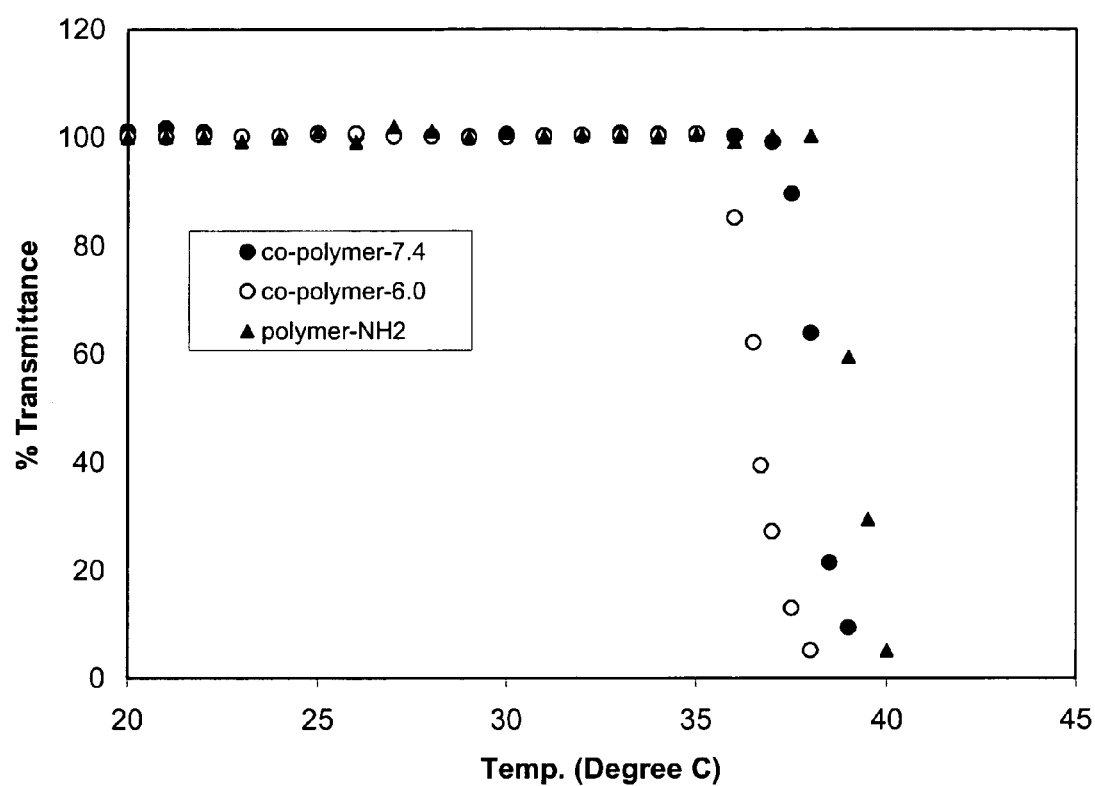
FIG. 31 shows the LCST measurements made of the block copolymers.

The synthesis of a block copolymer of polymer II was carried out by synthesizing the temperature sensitive/hydrophilic segment and pH sensitive fatty acid segment separately, and they were then conjugated to produce the block copolymer as shown in FIGS. 28 and 29 (Scheme 5 and 6). Briefly, the temperature sensitive segment was synthesized by reacting purified N-isopropylacrylamide) and N,N-dimethylacrylamide in a monomer ratio of 3.75:1.25, with 0.4 mol % of the chain transfer agent, 2-aminoethanethiol hydrochloride (AET.HCl) in 40 mL of alcohol in the presence of initiator azobisisobutyronitrile at 70° C. for 24 hrs. The polymer was purified by dissolving it in chloroform and precipitating it in diethyl ether. Molecular weight of the polymer was analyzed by GPC, and found to be Mw 11,221, On the other hand, poly(10-undecenoic acid) was synthesized by reacting the sodium salt of monomer (0.097 mol) in the presence of ammonium persulfate (0.8 g) in water at 70° C. for 24 hr. The polymer was precipitated in the presence of cold ethanol. Poly(10-undecenoic acid) was activated by NHS in the presence of DCC, and this product was further conjugated to temperature sensitive block in water at alkaline pH. Polymer molecular weight was Mw 29,177 (FIG. 30). The block co-polymer was analyzed for their pH and temperature sensitivity by measuring the LCST. As shown in FIG. 31, it is confirmed that the block co-polymer was indeed pH and temperature sensitive. The LCST of the block copolymer in PBS (pH 7.4) was 39.5° C., which reduced to 38.5° C. when blocked with poly(10-undecenoic acid). The block co-polymer exhibited a LCST of 36.7° C. at pH 6.0.

What is claimed is:

1. An amphiphilic copolymer comprising at least three types of monomeric units, said three types of monomeric units comprising:
   a temperature-sensitive monomeric unit,
   a hydrophilic monomeric unit, wherein the hydrophilic monomeric unit has one or more polar functionalities, and
   a hydrophobic monomeric unit comprising at least one pH-sensitive moiety;
   wherein said hydrophobic monomeric unit is derived from a copolymerisable unsaturated fatty acid,
   wherein said unsaturated fatty acid imparts hydrophobic character to the copolymer;
   wherein the copolymer has a lower critical solution temperature (LCST) dependent on environmental pH;
   wherein said lower critical solution temperature (LCST) decreases as pH decreases;
   wherein the fatty acid comprises 5 to 50 or more main chain carbon atoms;
   and wherein the fatty acid comprises at least 2 carbon-carbon double bonds (polyunsaturated).

2. The copolymer of claim 1, wherein the fatty acid is selected from the group consisting of (E,E)-9,12-Octadecadienoic Acid, (Z,Z)-9,12-Octadecadienoic Acid, (E,E)-9,11-Octadecadienoic Acid, (Z,Z,Z)-9,12,15-Octadecatrienoic Acid, (Z,Z,Z)-6,9,12-Octadecatrienoic Acid, (Z,Z,Z,Z)-6,9,12,15-Octadecatetraenoic Acid, (Z,Z,)-11,14-Ecosadienoic Acid, (Z,Z,Z)-5,8,11-Eicosatrienoic Acid, (Z,Z,Z)-11,14,17-Eicosatrienoic Acid, (Z,Z,Z)-8,11,14-Eicosatrienoic Acid, (Z,Z,Z,Z)-8,11,14,17-Eicosatetraenoic Acid, (Z,Z,Z,Z)-5,8,11,14-Eicosatetraenoic Acid, (Z,Z,Z,Z,Z)-5,8,11,14,17-Eicosapentaenoic Acid, (Z,Z)-13,16-Docosadienoic Acid, (Z,Z,Z)-13,16,19-Docosatrienoic Acid, (Z,Z,Z,Z)-7,10-13-16-Ocosatetraenoic Acid, (Z,Z,Z,Z)-4,7,10,13,16-Docosapentaenoic Acid, (Z,Z,Z,Z,Z)-7,10,13,16,19-Docosapentaenoic Acid, (Z,Z,Z,Z,Z,Z)-4,7,10,13,16,19-Docosahexaenoic Acid, and (Z,Z,Z,Z,Z,Z)-6,9,12,15,18,21-Tetracosahexaenoic Acid.

3. The copolymer of claim 1, wherein the temperature sensitive monomeric unit is derived from the group consisting of N-acroylpiperadine, N-t-butylacrylamide, N-piperidyl-methacrylamide and N-isopropylacrylamide.

4. The copolymer of claim 1, wherein the hydrophilic monomeric unit is derived from the group consisting of acrylic acid, acrylamide, acrylate, and substituted derivatives thereof.

5. The copolymer of claim 4, wherein the acrylamide is selected from the group consisting of acrylamide (AAm), N,N'-dimethylacrylamide (DMAAm), and N-(hydroxymethyl)acrylamide.

6. The copolymer of claim 1, further comprising a terminal group comprising at least one moiety selected from the group consisting of a terminating moiety, a ligand, a drug, a tag, a radioimmunoconjugate and a spacer.

7. The copolymer of claim 6, wherein the terminating moiety comprises a functional group selected from the group consisting of a hydroxyl group, a carboxyl group and an amino group.

8. The copolymer of claim 7, wherein the terminating moiety is introduced by chain transfer agents or group transfer agents.

9. The copolymer of claim 7, wherein the terminating moiety is introduced by living polymerisation methods.

10. The copolymer of claim 7, wherein the terminating moiety is part of the monomeric unit of the polymer.

11. The copolymer of claim 8, wherein the chain transfer agent is selected from the group consisting of chloroform, carbon tetrachloride, alkyl-mercaptans, aminoethanethiol, mercapto-propionic acid, mercapto-succinic acid, thioglycolic acid, mercaptoethanol and secondary alcohols thereof, alkyl halides, and salts of phosphorus acids with an oxidation number less than 5.

12. The copolymer of claim 11, wherein the aikyl-mercaptans are selected from the group consisting of octanethiol, decanethiol, n-dodecanethiol or t-dodecanethiol.

13. The copolymer of claim 6, wherein said ligand is attached to the functional group of the terminating moiety directly.

14. The copolymer of claim 6, wherein said ligand is attached to the terminating moiety by a spacer.

15. The copolymer of claim 14, wherein said spacer comprises more than 10 main chain atoms.

16. The copolymer of claim 15, wherein said ligand is selected from the group consisting of small targeting molecules, proteins, peptides and carbon hydrates.

17. The copolymer of claim 15, wherein the spacer comprises poly(ethylene glycol) and poly(propylene glycol).

18. The copolymer of claim 1, wherein the copolymer is a random copolymer.

19. A temperature and pH sensitive composition comprising:
a therapeutic agent, and the copolymer of claim 1 and wherein the fatty acid comprises 5 or more main chain carbon atoms.

20. The composition of claim 19, wherein the therapeutic agent is selected from the group consisting of an anticancer drug, an anti-inflammatory drug and a drug to treat neurological disorders.

21. The composition of claim 20, wherein the anticancer drug is selected from the group consisting of doxorubicin, anastrozole, exemestane, cyclophosphamide, epirubicin, toremifene, letrozole, trastuzumab, megestrol, nolvadex, paclitaxel, docetaxel, capecitabine, goserelin acetate, hydroxy urea, erythromycin, cyclosporin and cisplatin.

22. The composition of claim 19, wherein the molecular weight of the copolymer is less than 40,000 as determined by GPC.

23. The composition of claim 19, wherein the lower critical solution temperature of the copolymer is lower than 37° C. at a pH of less than 7.2.

24. The composition of claim 19, wherein the lower critical solution temperature of the conolymer is higher than 37° C. at a pH of 7.4 (normal physiological pH).

25. The composition of claim 19, wherein the mole ratio of temperature sensitive monomeric units to hydrophilic monomeric units to the hydrophobic monomeric units comprising at least one pH-sensitive moiety present in the copolymer is about 3.75 : 1.25 : 0.5.

26. A method of providing a selected therapeutic agent to an animal or human, comprising administering to said animal or human a temperature and pH-sensitive composition comprising:
a therapeutic agent, and the copolymer of claim 1.
wherein said copolymer is arranged into at least one nanoparticle comprising a hydrophobic core and a hydrophilic shell; and wherein said therapeutic agent is contained within said hydrophobic core.

27. The method of claim 26, wherein the composition is delivered orally.

28. The method of claim 26, wherein the composition is delivered locally.

29. The method of claim 26, wherein the composition is delivered intravenously.

30. The method of claim 26, wherein the composition is delivered tropically.

31. The method of claim 26, wherein the composition is delivered parenterally.

32. The method of claim 26, wherein the composition is delivered through inhalation.

33. The method of claim 26, wherein the composition is delivered through an ocular route.

34. An amphiphilic copolymer comprising at least three types of monomeric units, said three types of monomeric units comprising:
a temperature-sensitive monomeric unit,
a hydrophilic monomeric unit, wherein the hydrophilic monomeric unit has one or more polar functionalities, and
a hydrophobic monomeric unit comprising at least one pH-sensitive moiety;
wherein said hydrophobic monomeric unit is derived from a copolymerisable unsaturated fatty acid,
wherein said unsaturated fatty acid imparts hydrophobic character to the copolymer;
wherein the copolvmer has a lower critical solution temperature (LCST) dependent on environmental pH;
wherein said lower critical solution temperature (LCST) decreases as pH decreases; and
wherein the copolymer is a block copolymer.

35. The copolymer of claim 34, wherein the fatty acid comprises 5 to 50 main chain carbon atoms.

36. The copolymer of claim 35, wherein the fatty acid comprises at least 2 carbon-carbon double bonds (polyunsaturated).

37. The copolymer of claim 36, wherein the fatty acid is selected from the group consisting of (E,E)-9,12-Octadecadienoic Acid, (Z,Z)-9,12-Octadecadienoic Acid, (E,E)-9,11-Octadecadienoic Acid, (Z,Z,Z)-9,12,15-Octadecatrienoic Acid, (Z,Z,Z)-6,9,12-Octadecatrienoic Acid, (Z,Z,Z,Z)-6,9,12,1 5-Octadecatetraenoic Acid, (Z,Z,)-11,14-Ecosadienoic Acid, (Z,Z,Z)-5,8,11-Eicosatrienoic Acid, (Z,Z,Z)-11,14,17-

Eicosatrienoic Acid, (Z,Z,Z)-8,11,14-Eicosatrienoic Acid, (Z,Z,Z,Z)-8,11,14,17-Eicosatetraenoic Acid, (Z,Z,Z,Z)-5,8,11,14-Eicosatetraenoic Acid, (Z,Z,Z,Z,Z)-5,8,11,14,17-Eicosapentaenoic Acid, (Z,Z)-13,16-Docosadienoic Acid, (Z,Z,Z)-13,16,19-Docosatrienoic Acid, (Z,Z,Z,Z)-7,10-13-16-Ocasatetraenoic Acid, (Z,Z,Z,Z,Z)-4,7,10,13,16-Docosapentaenoic Acid, (Z,Z,Z,Z,Z)-7,10,13,16,19-Docosapentaenoic Acid, (Z,Z,Z,Z,Z,Z)-4,7,10,13,16,19-Docosahexaenoic Acid, and (Z,Z,Z,Z,Z,Z)-6,9,12,15,18,21-Tetracosahexaenoic Acid.

38. The copolymer of claim 34, wherein the temperature sensitive monomeric unit is derived from the group consisting of N-acroylpiperadine, N-t-butylacrylamide, N-piperidyl-methacrylamide and N-isopropylacrylamide.

39. The copolymer of claim 34, wherein the hydrophilic monomeric unit is derived from the group consisting of acrylic acid, acrylamide, acrylate, and substituted derivatives thereof.

40. The copolymer of claim 34, further comprising a terminal group comprising at least one moiety selected from the group consisting of a terminating moiety, a ligand, a drug, a tag, a radioimmunoconjugate and a spacer.

* * * * *